(12) United States Patent
McCoy et al.

(10) Patent No.: US 10,857,387 B2
(45) Date of Patent: Dec. 8, 2020

(54) BEAM PROFILE MEASUREMENT SYSTEM

(71) Applicant: ACCURAY INCORPORATED, Sunnyvale, CA (US)

(72) Inventors: Jonathan McCoy, Saratoga, CA (US); Atsushi Mitsuishi, Tokyo (JP); Hidetaka Koga, Tokyo (JP); Kazuyuki Kobayashi, Kanagawa (JP); Shigemi Ogawa, Tokyo (JP); Tadashi Otani, Kanagawa (JP)

(73) Assignee: ACCURAY INCORPORATED, Sunnyvale, CA (US)

( * ) Notice: Subject to any disclaimer, the term of this patent is extended or adjusted under 35 U.S.C. 154(b) by 176 days.

(21) Appl. No.: 15/446,170

(22) Filed: Mar. 1, 2017

(65) Prior Publication Data

US 2018/0250526 A1  Sep. 6, 2018

(51) Int. Cl.
*A61N 5/10* (2006.01)
*H01J 47/02* (2006.01)

(52) U.S. Cl.
CPC ......... *A61N 5/1048* (2013.01); *A61N 5/1075* (2013.01); *A61N 5/1077* (2013.01); *A61N 5/1083* (2013.01); *H01J 47/02* (2013.01); *A61N 2005/1076* (2013.01)

(58) Field of Classification Search
CPC ...... A61N 5/1048; A61N 5/1077; H01J 47/02
USPC .................................................... 250/252.1
See application file for complete search history.

(56) References Cited

U.S. PATENT DOCUMENTS

| | | | |
|---|---|---|---|
| 2005/0109939 A1 | 5/2005 | Engler et al. | |
| 2009/0250618 A1 | 10/2009 | Simon | |
| 2011/0022360 A1 | 1/2011 | Simon et al. | |
| 2011/0121164 A1 | 5/2011 | Navarro | |
| 2016/0077222 A1* | 3/2016 | Marsolat | G01T 1/26 250/370.07 |

OTHER PUBLICATIONS

Int'l Search Report and Written Opinion of the ISA/EP in PCT/US2018/020290 dated May 22, 2018; 11 pgs.
Commissioning @ QA for Tomotherapy, by Blue Phantom Helix, 2013, 3 pages.

(Continued)

*Primary Examiner* — David P Porta
*Assistant Examiner* — Gisselle M Gutierrez
(74) *Attorney, Agent, or Firm* — Womble Bond Dickinson (US) LLP

(57) ABSTRACT

A beam profile measurement (BPM) system is described including a BPM phantom including a tank to house liquid, a dosimeter disposed in the tank to detect ionization of a radiation beam emitted from a linear accelerator (LINAC), and a positioning device to move the dosimeter in a vertical direction. The BPM system also includes a BPM controller to operably couple to the BPM phantom and the LINAC. A method is described including positioning, using a BPM controller, a dosimeter of the BPM phantom in a first location, positioning, using the BPM controller, the LINAC in a second location, performing, using the BPM controller, a first movement of the LINAC from the second location to a third location, emitting a radiation beam from the LINAC during the first movement, and performing, via the dosimeter, an ion measurement of the radiation beam during the emitting.

16 Claims, 14 Drawing Sheets

(56) References Cited

OTHER PUBLICATIONS

Blue Phantom 2, 2015, myQA Accept, 5 pages.
3D Scanner—3D Scanning Comes Full Circle, Sun Nuclear Corporation, 2015, 12 pages.
Almond, P.R. et al. (Sep. 9, 1999) "AAPM's TG-51 Protocol for Clinical Reference Dosimetry of High-energy Photon and Electron Beams" Med. Phys. 26(9) 1847-1870.
Das, I.J. et al. (Sep. 9, 2008) "Accelerator Beam Data Commissioning Equipment and Procedures: Report of the TG-106 of the Therapy Physics Committee of the AAPM" Med. Phys. 35(9) 4185-4215.
Palta, Dr. J.R. "Dosimetrick Characteristics of Clinical Photon Beams" University of Florida, Department of Radiation Oncology, 53 pages.2002.
Automate Absorbed Dose to Water Measurements, Doseview 1D, 2016, 4 pages.
PTW Water Phantoms, (Sep. 18, 2016), Phantom Tank, 1 page.
Radiation Medcine QA Solutions, 2016, 164 pages.

\* cited by examiner

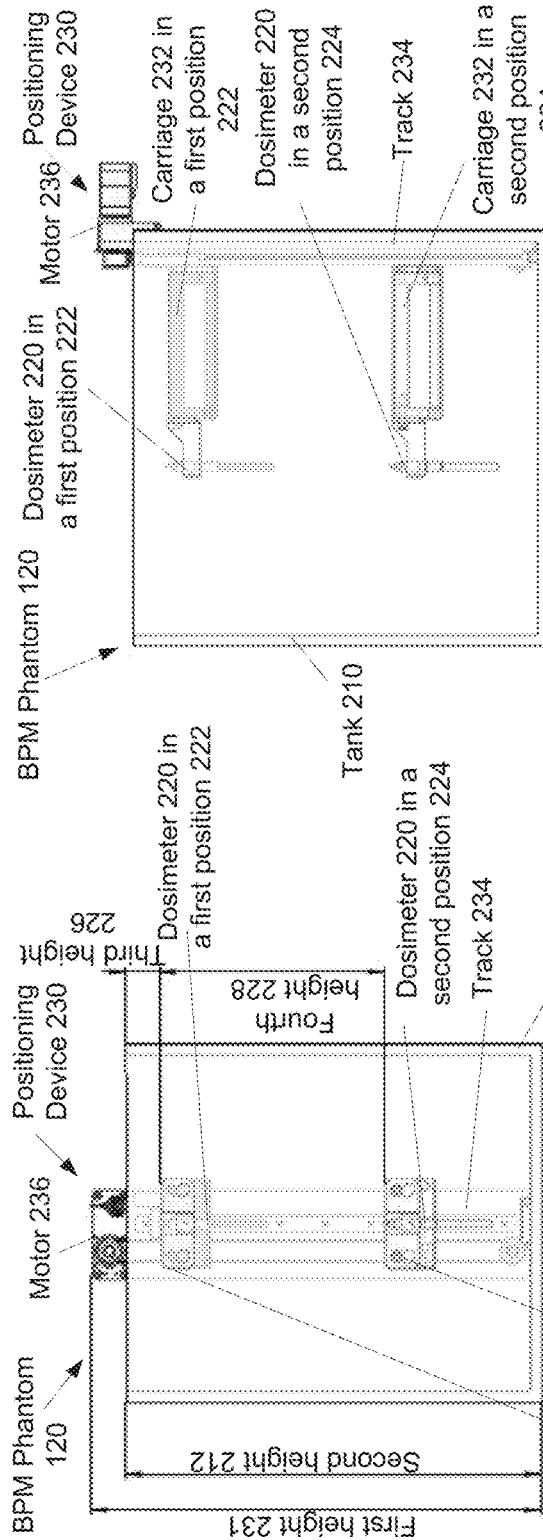
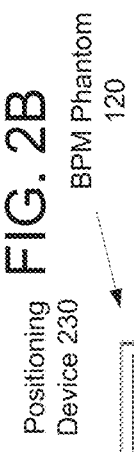
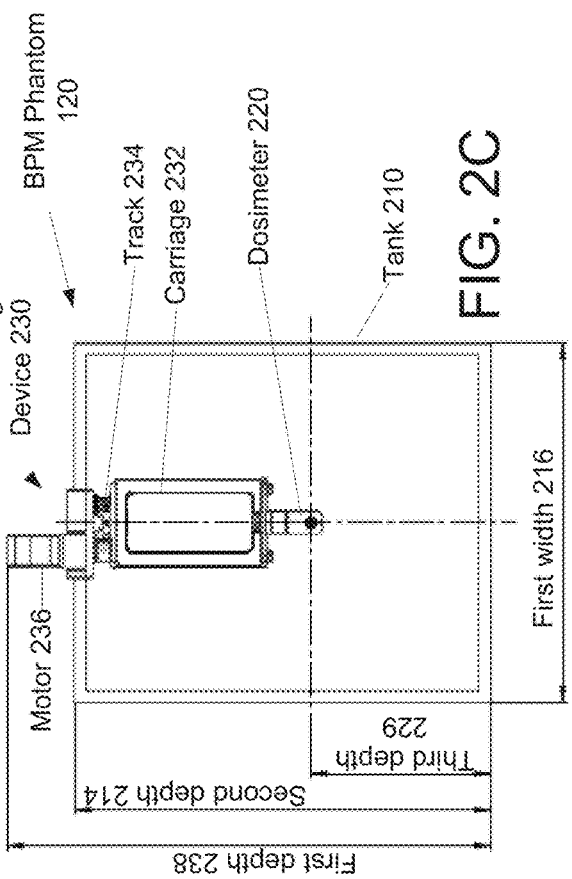
FIG. 2A
FIG. 2B
FIG. 2C

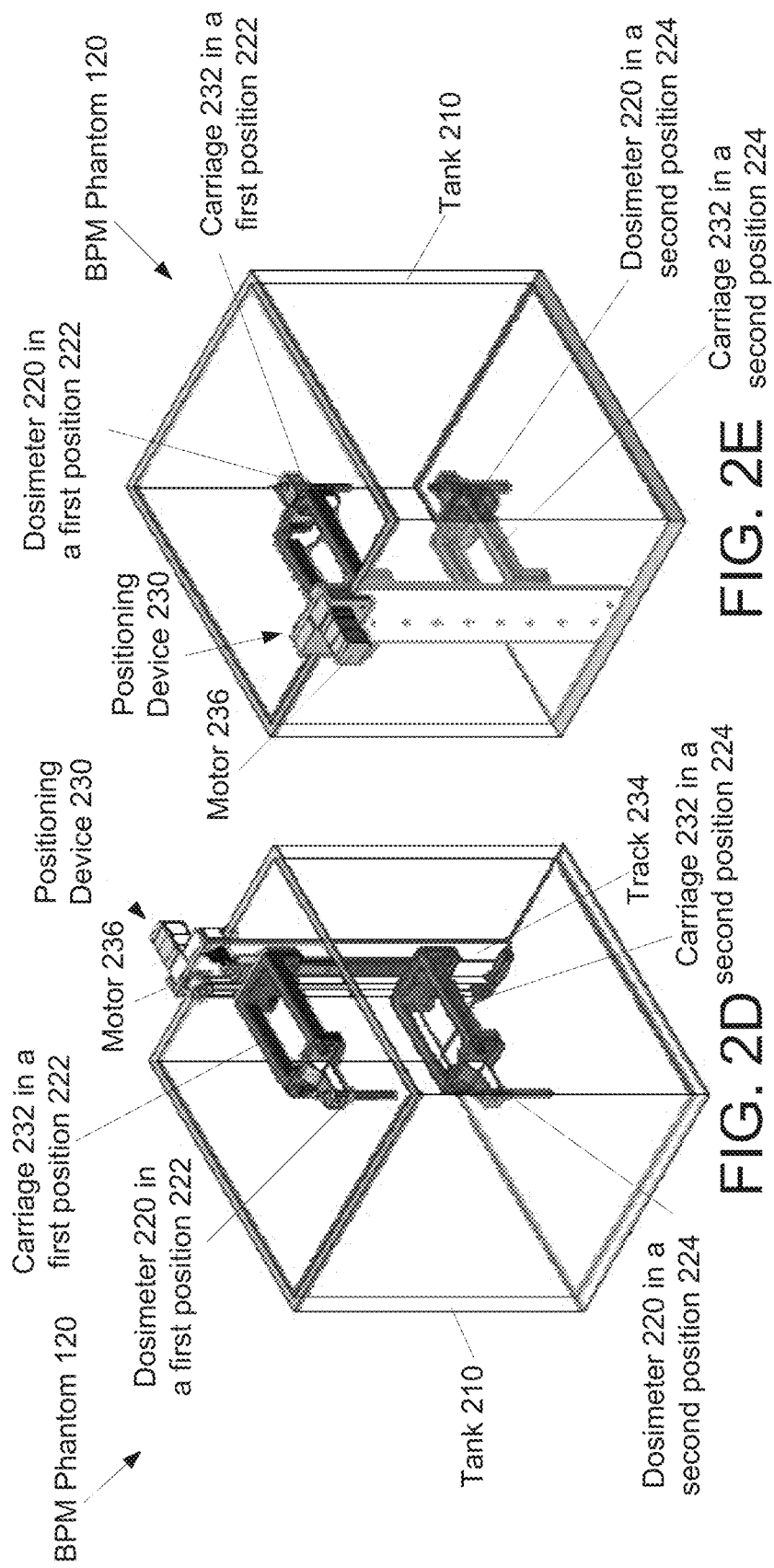

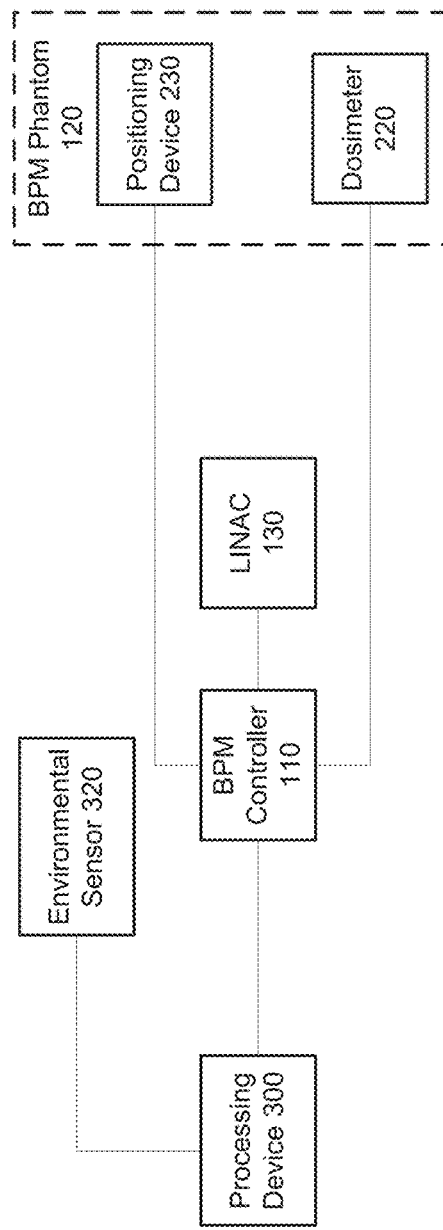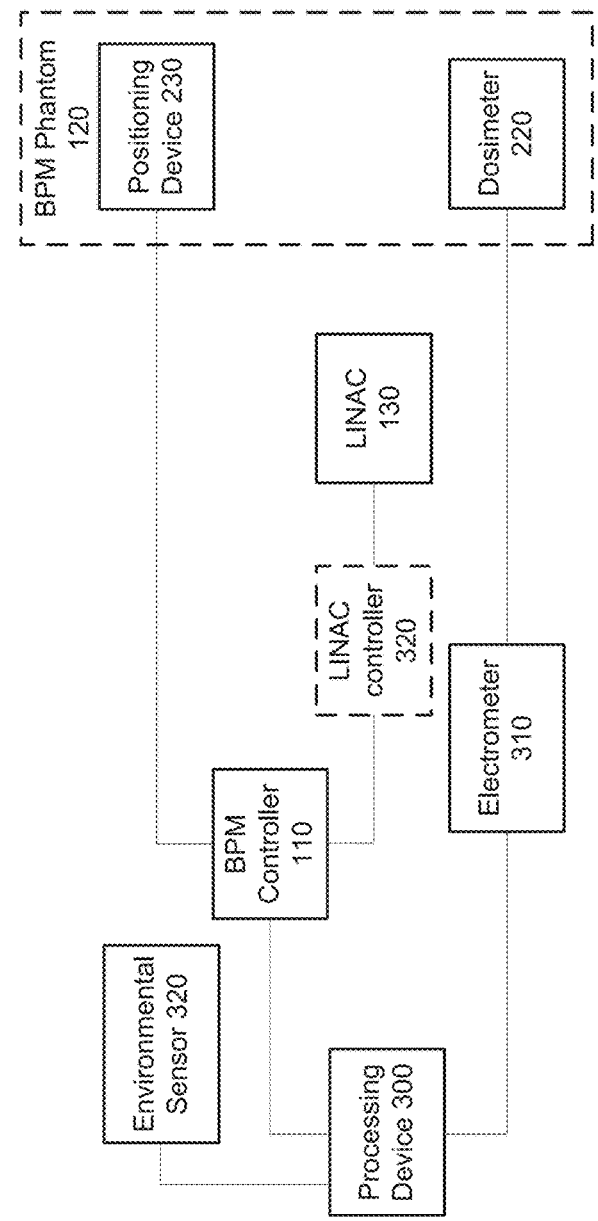

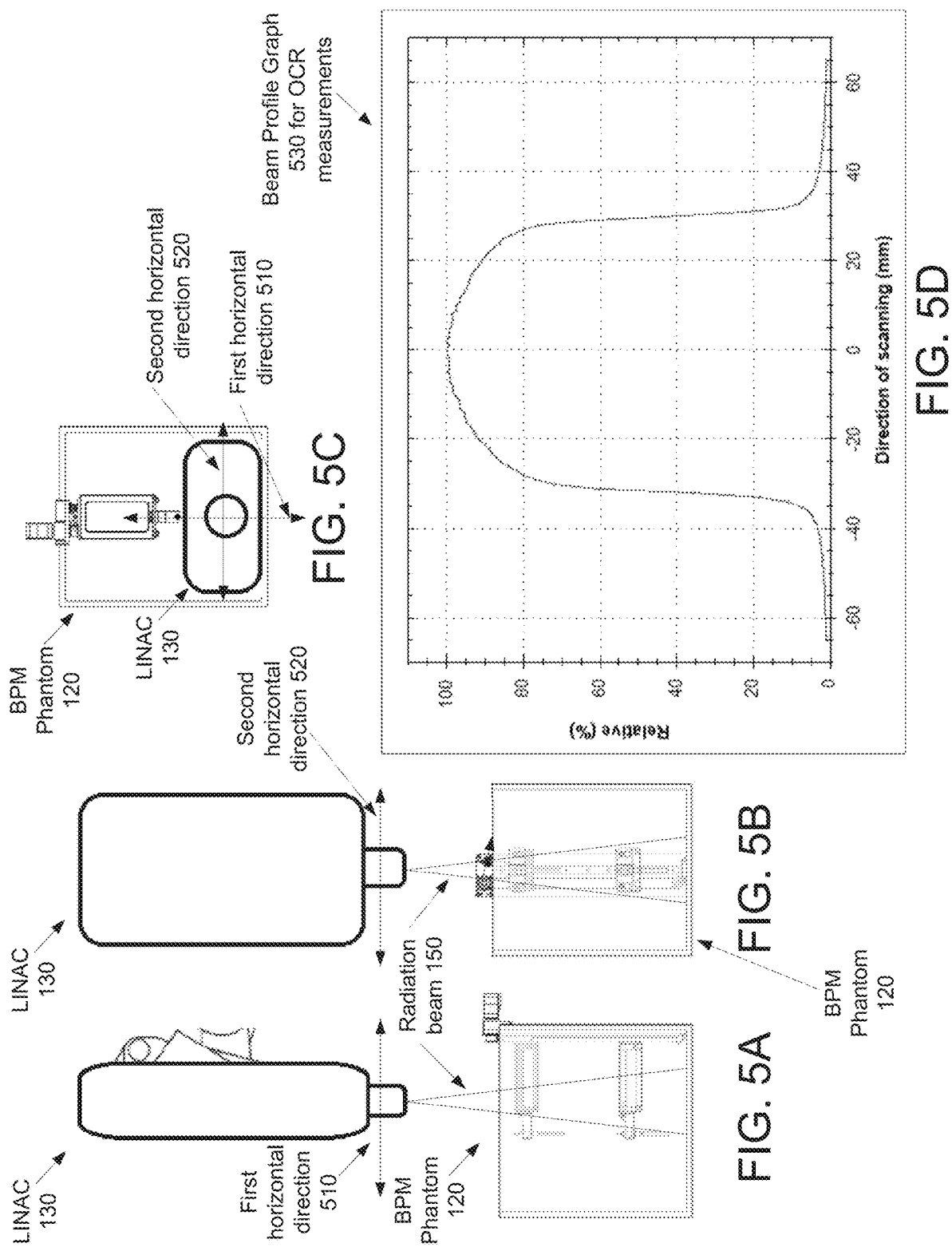

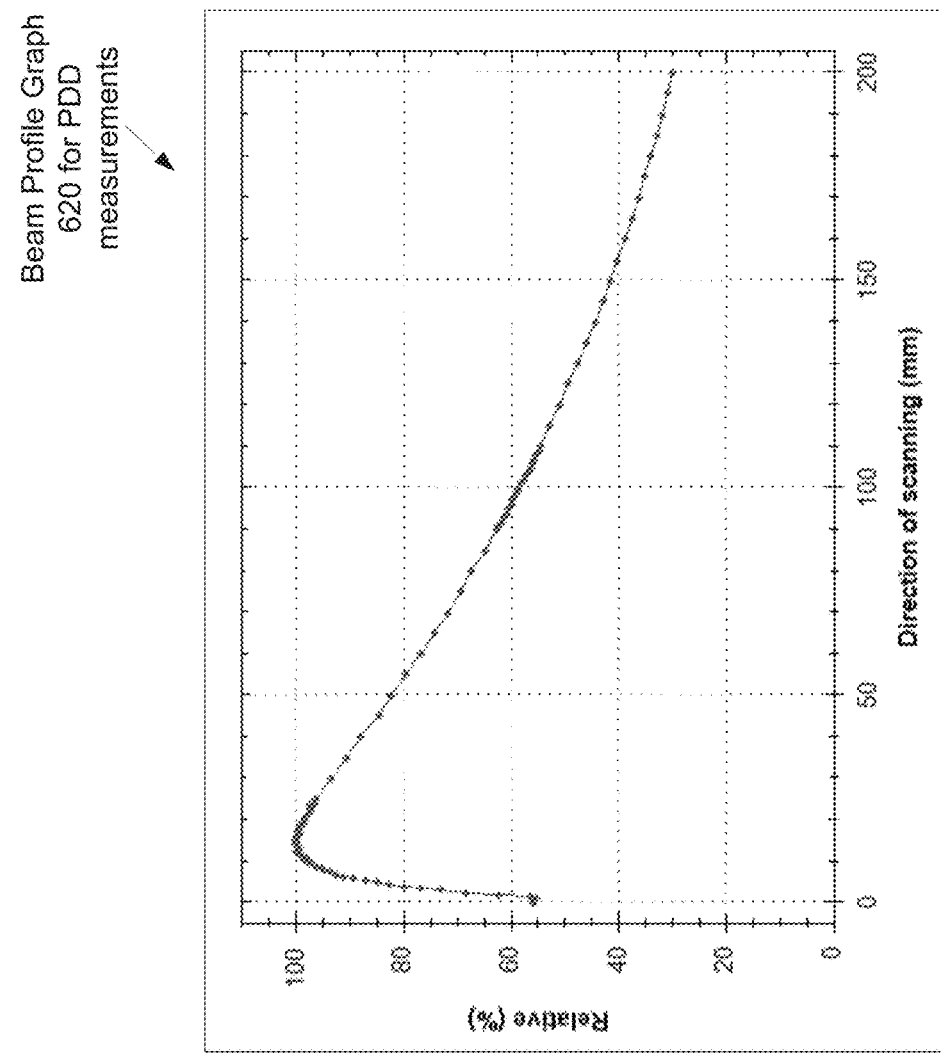
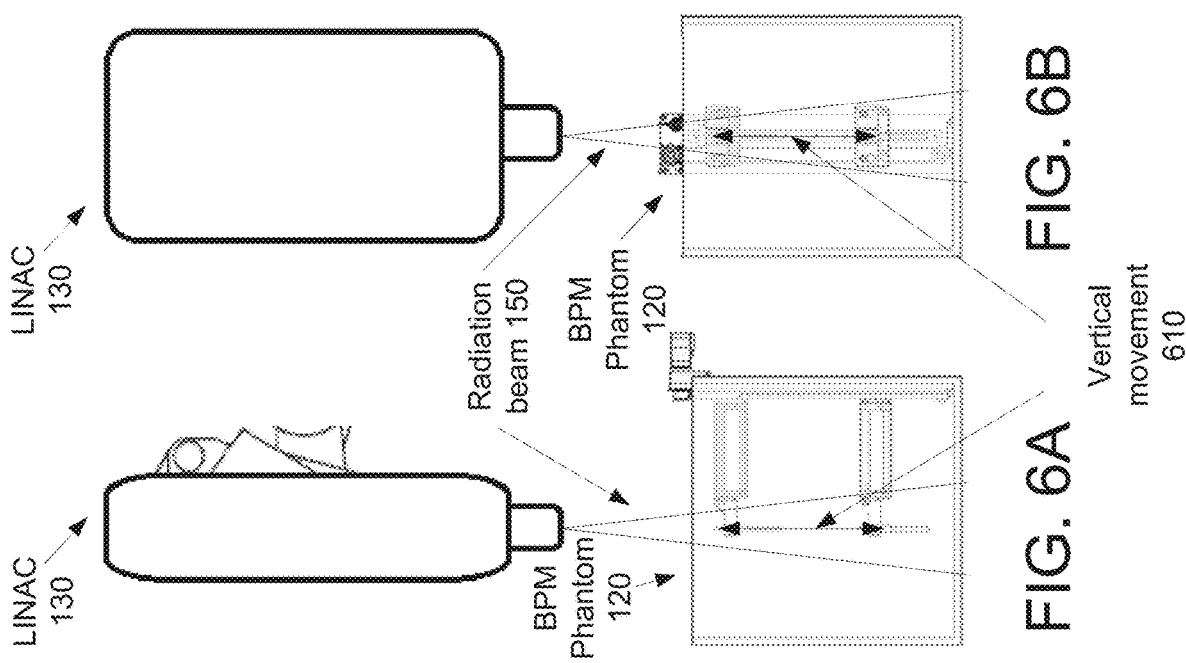
FIG. 6A  FIG. 6B
FIG. 6C

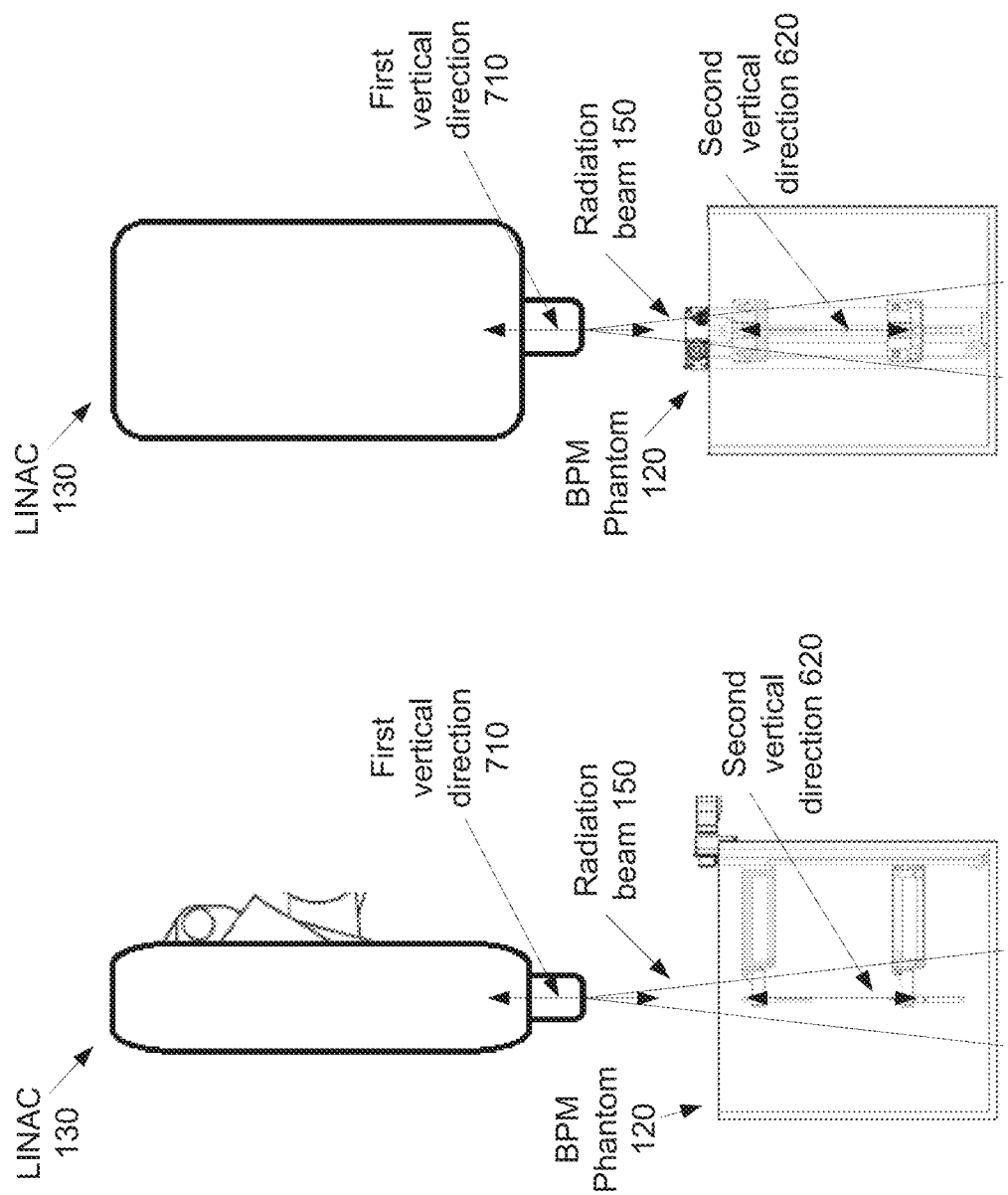

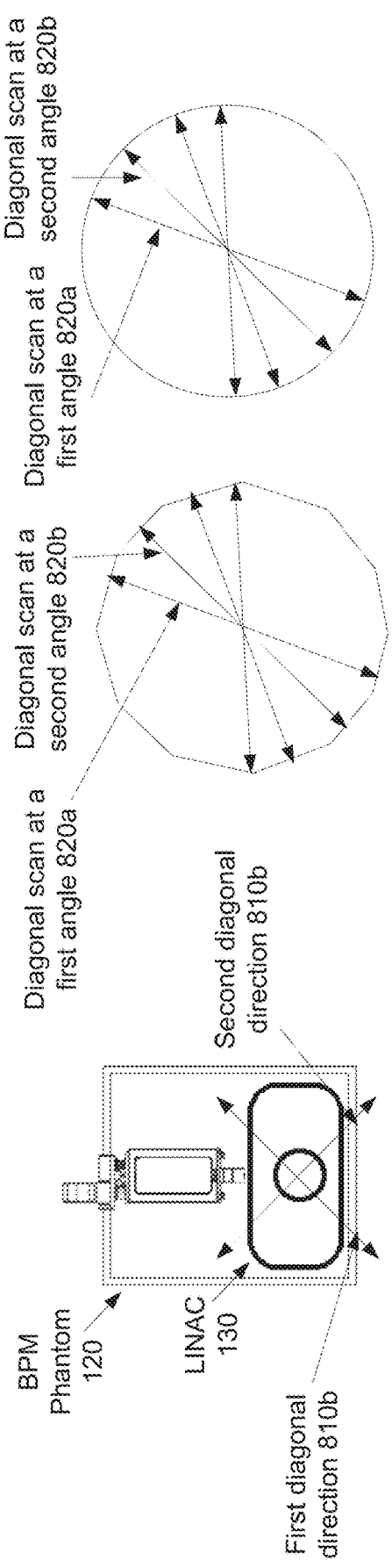
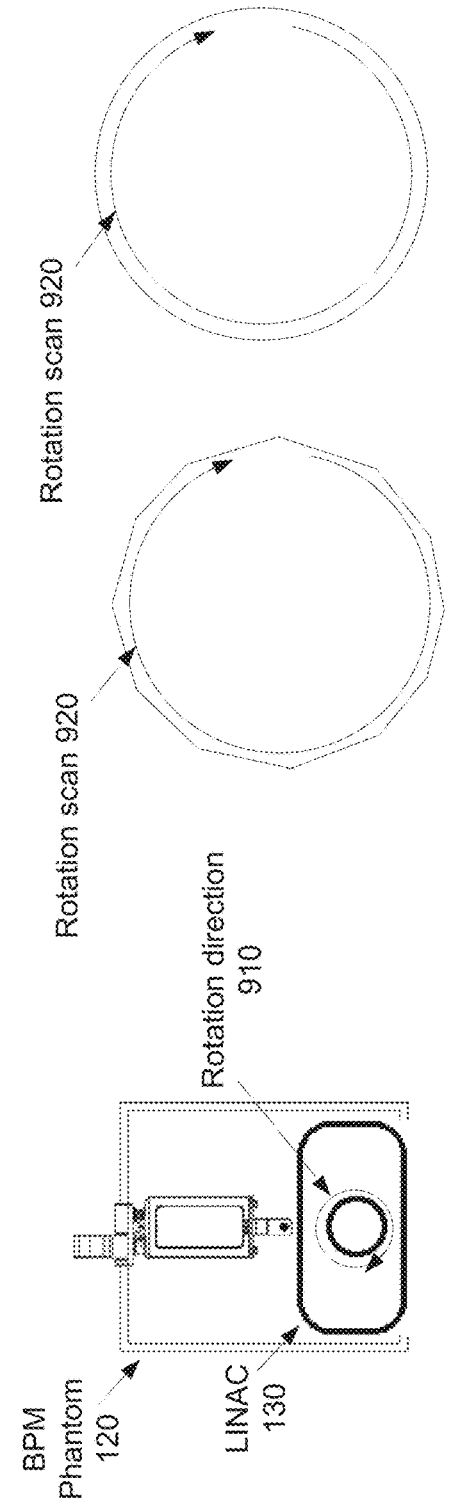

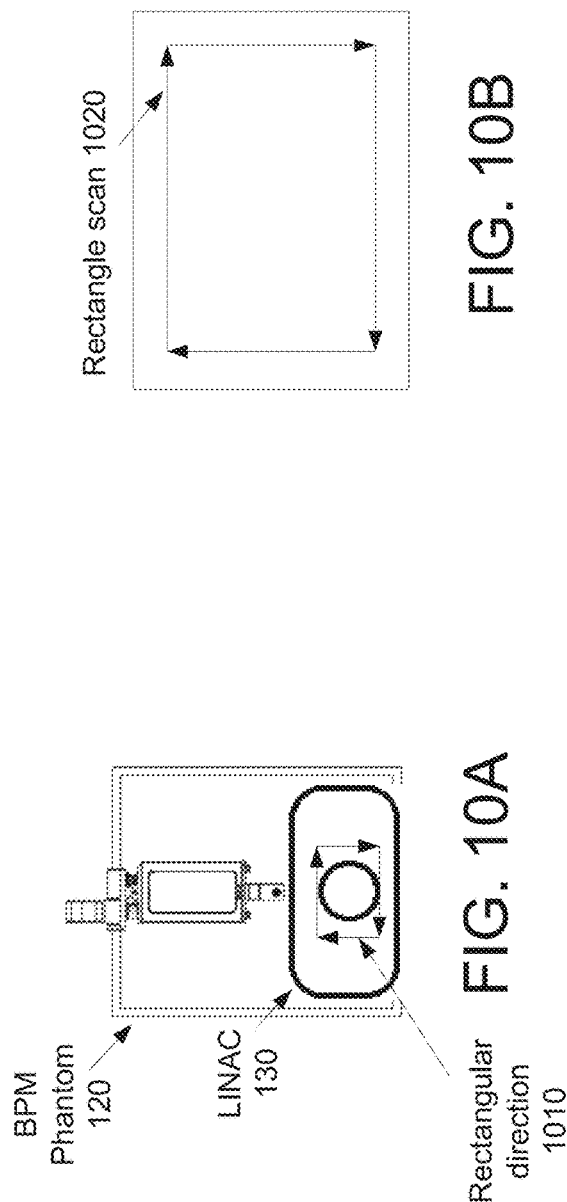
FIG. 10A
FIG. 10B
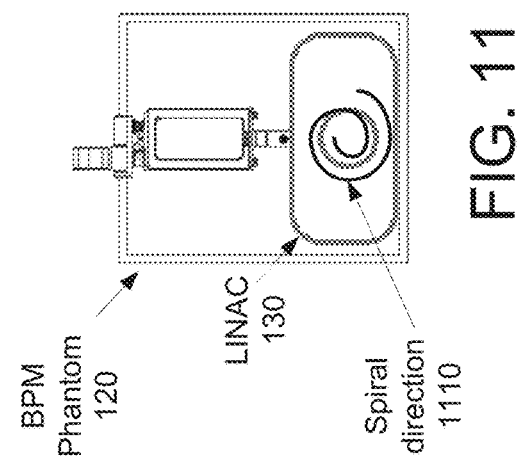
FIG. 11

BEAM PROFILE MEASUREMENT SYSTEM

TECHNICAL FIELD

Implementations of the present disclosure relate to a beam profile measurement (BPM) system.

BACKGROUND

A linear accelerator (LINAC) is used to emit a radiation beam to a target (e.g., a tumor within a patient) for radiation treatment. Before using a LINAC for the first time (e.g., for clinical use, etc.), the LINAC is commissioned (e.g., acceptance testing). Periodically (e.g., once a year), quality assurance (QA) is performed on the LINAC. Commissioning and QA can help avoid dosimetric and patient treatment errors that would otherwise lead to a poor treatment outcome.

There are many challenges for commissioning and QA, including the need for precision, a variety of testing methods, data validation, lack of standards, and time constraints. The commissioning and QA beam data may be treated as a reference and later used by treatment planning systems. As such, the collected data should be of the highest quality to avoid dosimetric and patient treatment errors. Task Group 106 (TG-106) of the Therapy Physics Committee of the American Association of Physicists in Medicine has given guidelines for properly measuring a set of beam data of the radiation beam emitted from a LINAC. In some implementations, the LINAC commissioning and QA beam data is to be compliant with the TG-106 guidelines.

Commissioning and QA of a LINAC may be performed by a system manufacturer of the LINAC, the purchasing site owner (e.g., an in-house physicist at a hospital), or a third party company. Traditionally, commissioning and QA involve not only the LINAC but also a dose measurement system (e.g., a phantom). A LINAC system has an internal dose measurement system that is calibrated to measure dose of a radiation beam emitted by the LINAC. For calibration, verification, and commissioning purposes, an external dose measurement system (reference system) is provided in addition to the internal dose measurement system. The external dose measurement system includes a phantom that includes a dosimeter (e.g., ion chamber, linear diode, etc.) located inside a tank that houses a liquid, solid, or gas. This disclosure references the tank housing a liquid, but it is understood that a solid or gas could be used (e.g., as a human analog). The dosimeter may be moved to different locations within the liquid, solid, or gas in the tank and may be used to take measurements of a radiation beam emitted from the LINAC. The external measurement system is not integrated within or coupled to the internal measurement system, thus commissioning and QA include multiple manual steps which make the measurement excessive in time and labor.

Traditionally, LINAC commissioning and QA are long manual processes that require the precise positioning of a traditional phantom and the positioning of the LINAC in multiple (e.g., more than one hundred) positions. A traditional phantom moves the dosimeter along one or more axes within the liquid, solid, or gas in the tank. Traditionally, for commissioning and QA, the LINAC is positioned by a LINAC controller and the dosimeter of the phantom is positioned by a traditional phantom system (e.g., hardware and software) that is not coupled to the LINAC controller. The traditional phantom system controls only the position of the dosimeter and receives, from the dosimeter, measurements of the radiation beam emitted from the LINAC. Since, in traditional systems, the LINAC and the phantom must be separately moved into correct positions before measurements can be performed, lengthy setup time (e.g., up to several hours) may result. Traditional setup operations include one or more of moving the LINAC into position, aligning the origin of the tank with the isocenter of the LINAC, orienting the water phantom to minimize moving parts (e.g., use the x-direction which moves the dosimeter along the arm instead of the y-direction that moves the entire arm), providing coarse positioning through a hand pendant, providing final minute adjustments by fine x- and y-movements and phantom rotation, leveling and aligning the tank with the beam axes, resetting at least one of the isocenter or the origin after switching dosimeters, etc.

A traditional phantom system may control the position of the dosimeter and move the dosimeter during measuring of a radiation beam. Since traditional phantom systems cannot position the LINAC and cannot move the LINAC during the measuring of a radiation beam, traditional systems are limited to measurements such as percentage-depth dose (PDD) and off-center ratio (OCR) measurements (e.g., moving the dosimeter while emitting the radiation beam and taking a measurement of the radiation beam). In one implementation, a traditional system may perform tissue-phantom ratio (TPR) measurements by manually adding or removing liquid, solid, or gas from the phantom. In another implementation, a traditional system may perform TPR measurements by fastening an attachment (e.g., a "cage" attachment) to the LINAC, where the attachment holds the dosimeter. The LINAC is positioned so that the dosimeter and at least a portion of the attachment are in the liquid, solid, or gas in the tank. The LINAC is manually moved which also moves the attachment and dosimeter so that the dosimeter is at different depths in the liquid, solid, or gas in the tank.

Since the LINAC and a traditional phantom are separately positioned and the LINAC remains stationary during the performing of the measurements, there are multiple measurements that a traditional system cannot perform.

BRIEF DESCRIPTION OF THE DRAWINGS

The present disclosure is illustrated by way of example, and not by way of limitation, in the figures of the accompanying drawings.

FIGS. 2A-E illustrate views of the BPM phantom, in accordance with implementations of the present disclosure.

FIGS. 3A-B illustrate systems that may be used in performing beam profiling, in accordance with implementations of the present disclosure.

FIGS. 5A-D illustrate performing an off-center ratio (OCR) measurement with the BPM system, in accordance with implementations of the present disclosure.

FIGS. 6A-C illustrate performing a percentage depth dose (PDD) measurement with the BPM system, in accordance with implementations of the present disclosure.

FIGS. 7A-B illustrate performing a tissue phantom ratio (TPR) measurement or a tissue-maximum ratio (TMR)

measurement with the BPM system, in accordance with implementations of the present disclosure.

FIGS. 8A-C illustrate performing a diagonal beam measurement with the BPM system, in accordance with implementations of the present disclosure.

FIGS. 9A-C illustrate performing a rotation scan measurement with the BPM system, in accordance with implementations of the present disclosure.

FIGS. 10A-B illustrate performing a rectangle scan measurement with the BPM system, in accordance with implementations of the present disclosure.

FIG. 11 illustrates performing a spiral scan measurement with the BPM system, in accordance with implementations of the present disclosure.

Figure 12:
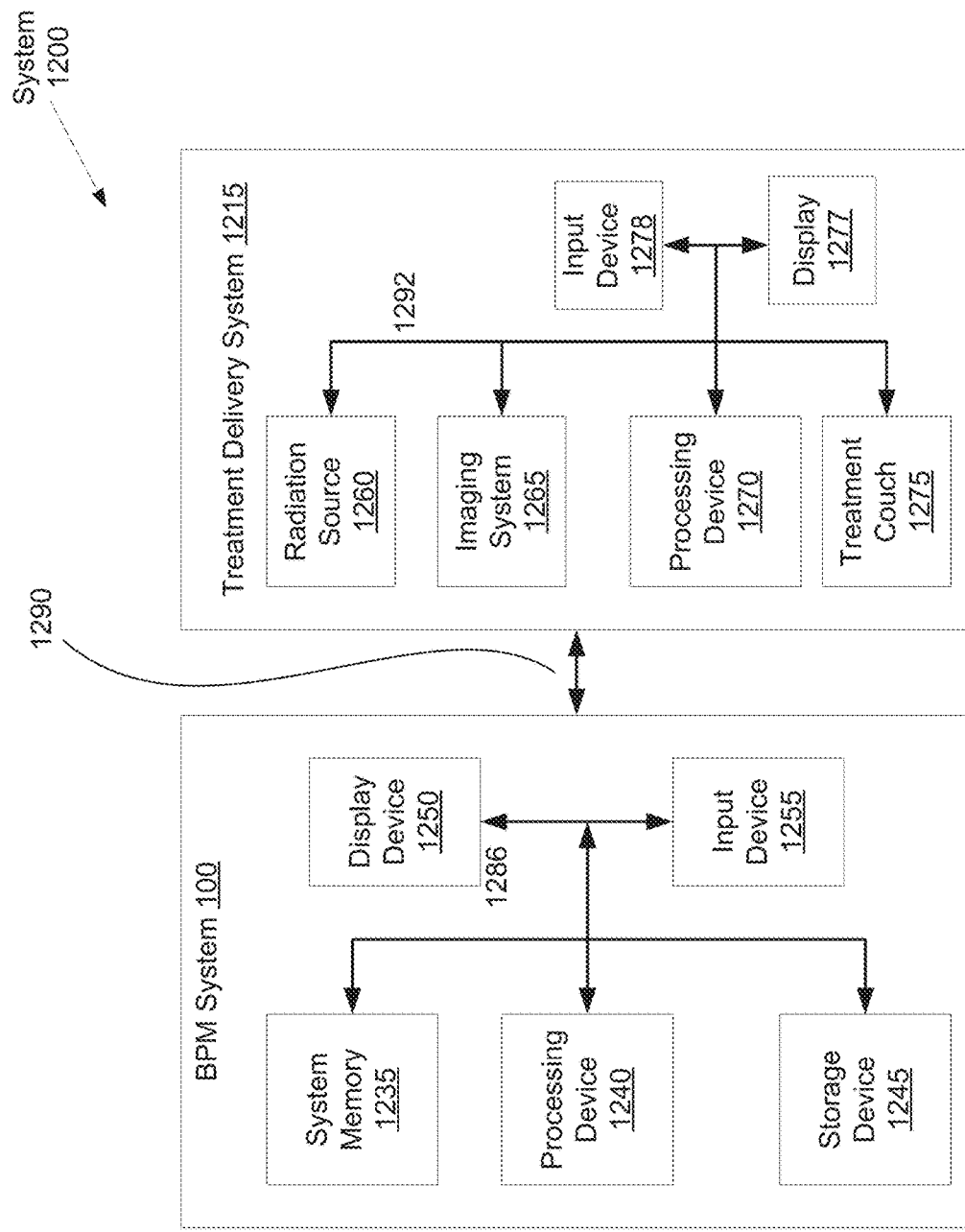

FIG. 12 illustrates systems that may be used in performing radiation treatment, in accordance with implementations of the present disclosure.

Figure 13:
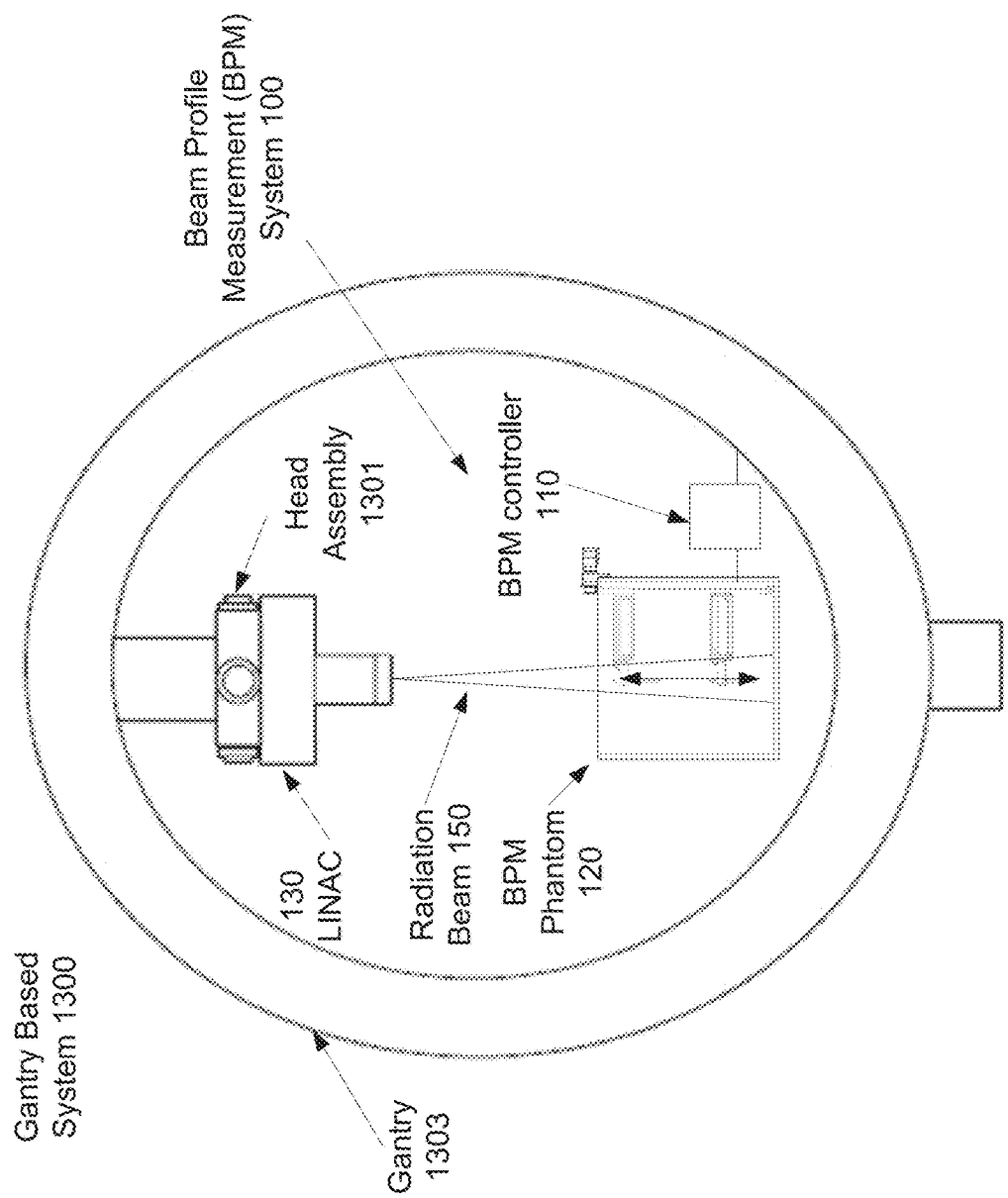

FIG. 13 illustrates a gantry based intensity modulated radiotherapy system, in accordance with implementations of the present disclosure.

Figure 14:
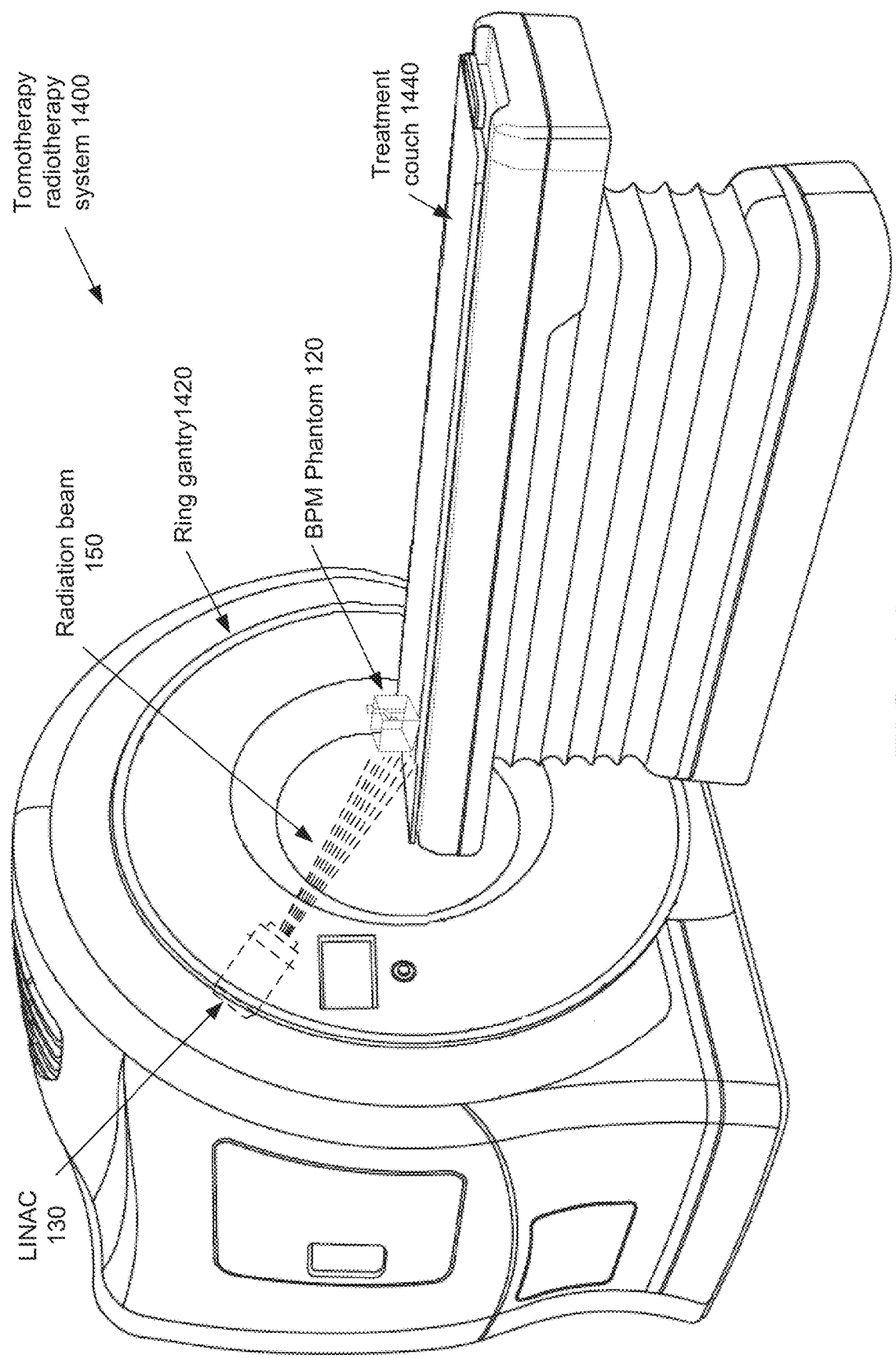

FIG. 14 illustrates a tomotherapy radiotherapy system, in accordance with implementations of the present disclosure.

DETAILED DESCRIPTION

Described herein are BPM systems and methods of use that, in some implementations, address the above and other deficiencies by controlling both a BPM phantom and the LINAC by using a BPM controller (e.g., the BPM controller is to operably couple to the BPM phantom and the LINAC). The BPM controller integrates the internal dose measurement system and the external dose measurement system via hardware and software (e.g., application software to control and monitor the corresponding devices). The BPM controller may position the dosimeter and the LINAC, perform a movement of at least one of the LINAC or the dosimeter while emitting a radiation beam using the LINAC during the movement and receive a measurement of the radiation beam during the movement from the dosimeter. Advantages of implementations of the BPM system disclosed herein may include reducing setup time (e.g., compared to a traditional BPM phantom system, BPM system disclosed herein may have a setup time of about 10 minutes) by positioning both the dosimeter and LINAC using the BPM controller. Other advantages may also include, for example, performing additional measurements by the BPM system disclosed herein (e.g., compared to the traditional BPM phantom system) by moving at least one of the LINAC or the dosimeter while emitting the radiation beam and performing measurements. Other advantages include substantially reducing knowledge and skills required by the operator and producing more consistent results.

Figure 1:
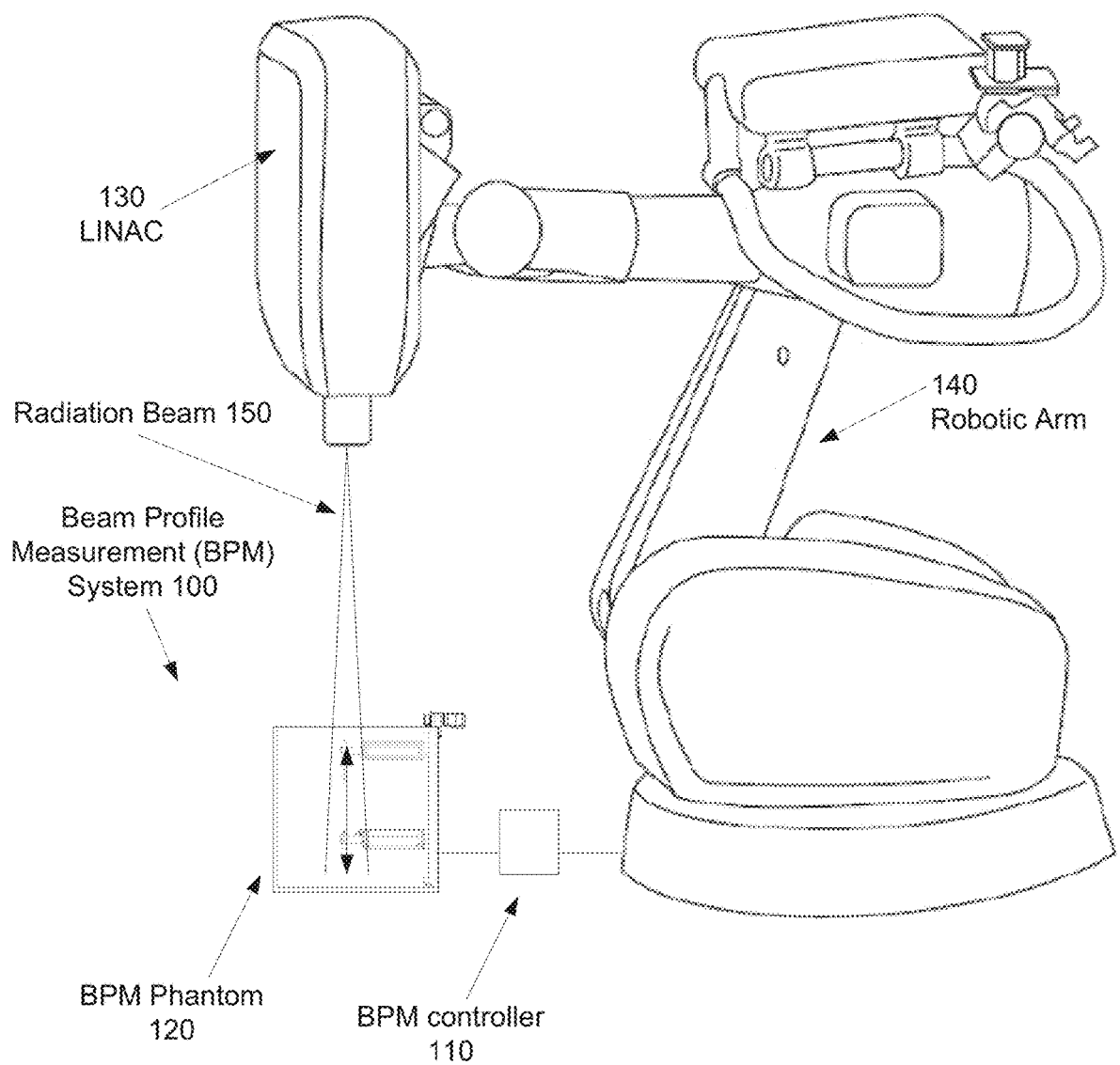
FIG. 1 illustrates components of a BPM system having a BPM controller and a BPM phantom, in accordance with implementations of the present disclosure.

FIG. 1 illustrates components of a BPM system 100 having a BPM controller 110 and a BPM phantom 120, in accordance with implementations of the present disclosure. The BPM controller 110 is coupled to the BPM phantom 120 and a LINAC 130. The LINAC 130 is mounted on a robotic arm 140 (e.g., LINAC 130 is robot-based). The robotic arm 140 moves the LINAC 130 in one or more of horizontal, vertical, diagonal, spiral, rectangular, circular, etc. directions. The LINAC 130 is positioned to emit a radiation beam 150 to the BPM phantom 120.

In alternative implementations, the methods described herein may be used with other types of phantoms, other types of LINACs, and other types of BPM systems. In one implementation, the BPM system 100 is coupled to a frameless robotic radiosurgery system (e.g., CyberKnife®). In another implementation, the BPM system 100 is coupled to a gantry-based LINAC treatment system where, for example, LINAC 130 is coupled to a gantry 1303 of gantry based system 1300 of FIG. 13. Alternatively, BPM system 100 may be used with other types of radiation treatment systems, for example, a tomotherapy system as illustrated in FIG. 14.

FIGS. 2A-E illustrate views of the BPM phantom 120, in accordance with implementations of the present disclosure. FIG. 2A is a front view, FIG. 2B is a side view, FIG. 2C is a top view, FIG. 2D is a front perspective view, and FIG. 2E is a back perspective view of the BPM phantom 120, in accordance with implementations of the present disclosure. BPM phantom 120 includes a tank 210, a dosimeter 220, and a positioning device 230.

The tank 210 includes a liquid (e.g., water), solid, or gas (e.g., acting as a human analog) during emitting of the radiation beam 150 using the LINAC 130 and performing of measurements by the dosimeter 220. The tank 210 includes a bottom wall, a front wall, a back wall, a first side wall, and a second side wall. The upper surface of tank 210 is open (e.g., no upper wall). In one implementation, the tank 210 may have a second height 212 of about 370 millimeters (mm) (outer surface of bottom wall of tank 210 to top surface of tank 210), a second depth 214 of about 370 mm (outer surface of front wall of tank 210 to outer surface of back wall of tank 210), and a first width 216 of about 320 mm (outer surface of first side wall of tank 210 to outer surface of second side wall of tank 210). In another implementation, the tank 210 may have outer dimensions of 10"×10"×10" or less. In one implementation, the tank 210 has a second height 212 of about 300 mm.

The dosimeter 220 is one or more of an ionization chamber (ion chamber), linear diode, detector, diode detector, etc. In one implementation, the BPM phantom 120 includes dosimeter 220 that is movable only in a vertical direction. FIGS. 2A-B and D-E display a first position 222 and a second position 224 (e.g., two potential positions) of the dosimeter 220. In one implementation, the first position 222 may be a maximum height of the dosimeter 220 relative to the tank 210 and the second position 224 may be a minimum height of the dosimeter 220 relative to the tank 210. The dosimeter 220 is located in any position from maximum height (e.g., first position 222) to the minimum height (e.g., second position 224). During emitting of the radiation beam 150 and performing measurements, the tank 210 is filled with liquid, solid, or gas so that the dosimeter 220 is fully submerged in the liquid, solid, or gas. During emitting of the radiation beam 150 and performing measurements, the dosimeter 220 is stationary or moving in the vertical direction (see FIGS. 5A-11). In one implementation, the dosimeter 220 may have a third depth 229 of about 160 mm from the front surface of the tank 210 to the center of the dosimeter 220 (see FIG. 2C).

The positioning device 230 is utilized to move the dosimeter in the vertical direction. The positioning device 230 includes one or more of a motorized carriage, a drive shaft, a motor, a belt, a drive shaft, etc. The positioning device 230 includes a carriage 232 coupled to a track 234 that is coupled to a motor 236. In one implementation, the motor 236 is coupled to a belt that moves the carriage 232 in a vertical direction along the track 234. In another implementation, the motor is coupled to a drive shaft that moves the carriage 232 in a vertical direction along the track 234. The carriage 232 secures the dosimeter 220. The carriage 232 and track 234 are located inside the tank 210 and the motor 236 is located exterior to (e.g., above) the tank 210. The motor 236 moves the carriage 232 along the track 234 (e.g., which moves the dosimeter 220). In one implementation, the positioning device 230 is used to move the dosimeter 220 from about 15 mm to about 200 mm below an upper surface of the liquid, solid, or gas in the tank 210. In one implementation, the positioning device 230 only moves the dosimeter 220 along one vertical axis which provides less disturbance to the liquid, solid, or gas in the tank 210 (e.g., water wavering, liquid or solid or gas surface movement) than with a positioning device that moves a dosimeter 220 along more than one axis.

In one implementation, the BPM phantom 120 may have a first height 231 of about 401 mm from the outer surface of the bottom wall of the tank 210 to the top surface of the positioning device 230 (see FIG. 2A) and a first depth 238 of about 430 mm from the outer surface of the front wall of the tank 210 to the back surface of the positioning device 230 (e.g., back surface of motor 236; see FIG. 2C). The carriage 232 in the first position 222 may have a third height of about 30 mm from the top of the carriage 232 in the first position 222 to the top surface of the tank 210 (see FIG. 2A). The carriage 232 in the second position 224 may have a fourth height of about 200 mm from the top of the carriage 232 in the second position 224 to the top of the carriage 232 in the first position 222 (see FIG. 2A).

FIGS. 3A-B illustrate systems that are used in performing beam profiling, in accordance with implementations of the present disclosure.

Referring to FIG. 3A, a processing device 300 is coupled with BPM controller 110. BPM operation software operates on the processing device 300 to control the BPM controller 110. BPM controller 110 is coupled to the BPM phantom 120 and the LINAC 130 (see FIG. 1). The BPM phantom 120 includes positioning device 230 and dosimeter 220 (see FIG. 2A-E). Specifically, the BPM controller 110 is coupled to the LINAC 130, positioning device 230, and dosimeter 220 (see FIGS. 2A-E). The BPM controller 110 is operably coupled to the BPM phantom 120 and the LINAC 130, where the BPM controller 110 positions the dosimeter 220 in a first location, positions the LINAC 130 in a second location, performs a first movement of the LINAC 130 from the second location to a third location, emits the radiation beam 150 using the LINAC 130 during the first movement, and receives, from the dosimeter 220, an ion measurement of the radiation beam 150 during the first movement.

One or more of the processor 300, BPM controller 110, or LINAC 130 is coupled to one or more environmental sensors 320. The BPM controller 110 or processor 300 receives one or more ambient pressure and temperature measurements from the one or more environmental sensors 320. The BPM controller 110 or processor 300 adjusts the ion measurement of the radiation beam 150 received from the dosimeter 220 in view of the one or more ambient pressure and temperature measurements. The BPM controller 110 or processor 300 receives one or more location measurements of the LINAC 130 relative to the BPM system (e.g., distance between LINAC 130 and BPM controller 110, LINAC 130 and processing device 300, LINAC 130 and BPM phantom 120, LINAC 130 and positioning device 230, LINAC 130 and dosimeter 220, etc.) from the one or more environmental sensors 320. The positioning of the LINAC 130 is in view of the one or more location measurements. The BPM controller 110 may perform setup of the BPM phantom 120 and LINAC 130 in view of the location measurements from the one or more environmental sensors 320.

The environmental sensor 320 may include one or more of a pressure sensor, a temperature sensor, a barometric temperature sensor, a GPS-pressure-temperature sensor, a sensor that measures pressure and temperature (e.g., supply temperature and pressure), relative presence of each component (e.g., distance between LINAC 130 and BPM controller 110, LINAC 130 and processing device 300, LINAC 130 and BPM phantom 120, LINAC 130 and positioning device 230, LINAC 130 and dosimeter 220, etc.), leveling information of a component (e.g., if the LINAC 130 is level, if the BPM phantom 120 is level, if the dosimeter 220 is level, if the positioning device 230 is level, etc.), leveling information of a first component relative to a second component (e.g., if a surface of the LINAC 130 is parallel to a surface of the BPM phantom 120, etc.), etc. The environmental sensor 320 may be coupled to a microcontroller coupled to an interface that couples to the processing device 300, BPM controller 110, or LINAC 130. The digital signal may have a +/−1 hectopascal (hPa) (millibar (mbar)) absolute accuracy in pressure and 0.5 degree Celsius (C) for temperature and may have a 0.02% error centigray (cGy) estimate.

Referring to FIG. 3B, a processing device 300 is coupled with BPM controller 110, environmental sensor 320, and electrometer 310. BPM operation software operates on the processing device 300 to control the BPM controller 110 and the electrometer 310.

The electrometer 310 is coupled with the dosimeter 220 of BPM phantom 120. The electrometer 310 amplifies the amount of ionization detected by the dosimeter 220. The electrometer 310 provides a hardware interface (e.g., Ethernet interface, RS-232C interface, etc.) for an external device control and a protocol that specifies a set of commands that can be used to setup devices, control devices, and monitor measurements (e.g., software). In one implementation, a software application programming interface (API) may implement one or more of the set of commands of the protocol. The high voltage sense (plus or minus) of the electrometer 310 may be automatically changed (e.g., not manually switched) so that activities (e.g., TG-51) that require changing of the high voltage sense can be fully automated. The electrometer 310 may allow for changing the voltage amplitude and sign of the voltage of the electrometer 310 (e.g., as required by TG-51) (e.g., setting up the electrometer high voltage including its sense).

BPM controller 110 is coupled to the positioning device 230 of BPM phantom 120 and the LINAC 130. In one implementation, the BPM controller 110 is coupled to LINAC controller 320 which is coupled with LINAC 130. The LINAC controller 320 controls one or more of the position of the LINAC 130, the emitting of a radiation beam 150 using the LINAC 130, the movement of the LINAC 130, etc. The BPM controller 110 controls the LINAC 130 via the LINAC controller 320. The BPM controller 110 is operably coupled to the BPM phantom 120 and the LINAC 130, where the BPM controller 110 positions the dosimeter 220 in a first location, positions the LINAC 130 in a second location, performs a first movement of the LINAC 130 from the second location to a third location, emits the radiation beam 150 using the LINAC 130 during the first movement, and receives, from the dosimeter 220, an ion measurement of the radiation beam 150 during the first movement. The BPM controller 110 receives the ion measurement via the processing device 300 and the electrometer 310.

In one implementation, the processing device 300 may perform a fully software-controlled (not performed manually) data collection of different measurements including one or more of OCR, PDD, TPR, TMR, diagonal beam, rotation scan, rectangle scan, spiral scan, Task Group 51 (TG-51), Task Group 135 (TG-135), etc. The processing device 300 may perform the different measurements when different collimator sizes and types are coupled to LINAC 130. The processing device 300 may have integrated into a single process the control of the robotic arm 140, LINAC 130, dosimeter 220, positioning device 230, and environmental sensors 320 to automate data collection of the radiation beam 150. The processing device 300 may provide communication between the BPM phantom 120 (e.g., dosimeter 220 and positioning device 230) and the LINAC system (e.g., robotic arm 140 and LINAC 130). The data collection may be an automatic dose measurement that encapsulates dose measurement activities (e.g., performed by on site physicists, performed by the LINAC manufacturer, etc.).

In one implementation, the BPM operation software includes a graphical use interface (GUI) to measure the dose, a first command line utility to calibrate the dose, and a second command line utility to measure the dose consistency. The GUI may be an extension of a software application to operate the LINAC 130. The GUI may include support for the electrometer 310 and the environmental sensor 320. The environmental sensor 320 may be used or temperature and pressure values may be manually entered. Upon initialization of the GUI, the electrometer 310 is properly setup. As a radiation beam 150 is being delivered, the GUI displays the internally measured amount of dose of the radiation beam 150 and the externally (reference) measured amount of dose of the radiation beam 150 (e.g., amount of dose as it has been measured by the electrometer 310 coupled to the dosimeter 220). The GUI also displays absolute and relative difference (error) between the internal and reference dose measurements.

The first command line utility runs 10, 30, 50, 100, and 200 nominal monitor units (MUs) (a measure of machine output from a LINAC 130 as measured by dosimeter 220) and measures what the electrometer 310 reports. Once the measurements have completed, the first command line utility calculates the model parameters (e.g., gain) for each dose channel and stores the model parameters in a corresponding data file. The first command line utility performs the calibration of the dose automatically (e.g., not manually).

The second command line utility tests dose consistency when pre-delivery conditions change. Dose amount measurements depend on the state of the LINAC 130 before the measurement has started. For example, the measurements may depend on whether a high voltage (e.g., high voltage and the radiation beam 150) were activated. The measurements also depend on the length of period between emitting a first radiation beam and emitting a second radiation beam. The second command line utility may determine if the LINAC 130, the internal dose measurement system, (imaging system coupled to LINAC 130) or the external (reference) dose measurement system (BPM system 100) is malfunctioning. A test procedure may include verifying the LINAC 130 is calibrated and that the equipment is properly setup, running a sequence of 20 radiation beams (each 100 cGy) with no delay between the beams, waiting two hours with high voltage and the radiation beam off, running a sequence of 20 radiation beams (each 100 cGy) with no delay between the beams, wait two hours with high voltage on and beam off, running a sequence of 20 radiation beams (each 100 cGy) with no delay between the beams, and wait two hours with high voltage on and beam on. The test procedure runs four sequences of 20 radiation beams and has three 2-hour delays. Each delay has different conditions regarding high voltage and the radiation beam and each measurement following a respective delay may have a different absolute error (cGy), therefore the conditions during the delay may affect the measurements.

Figure 4A:
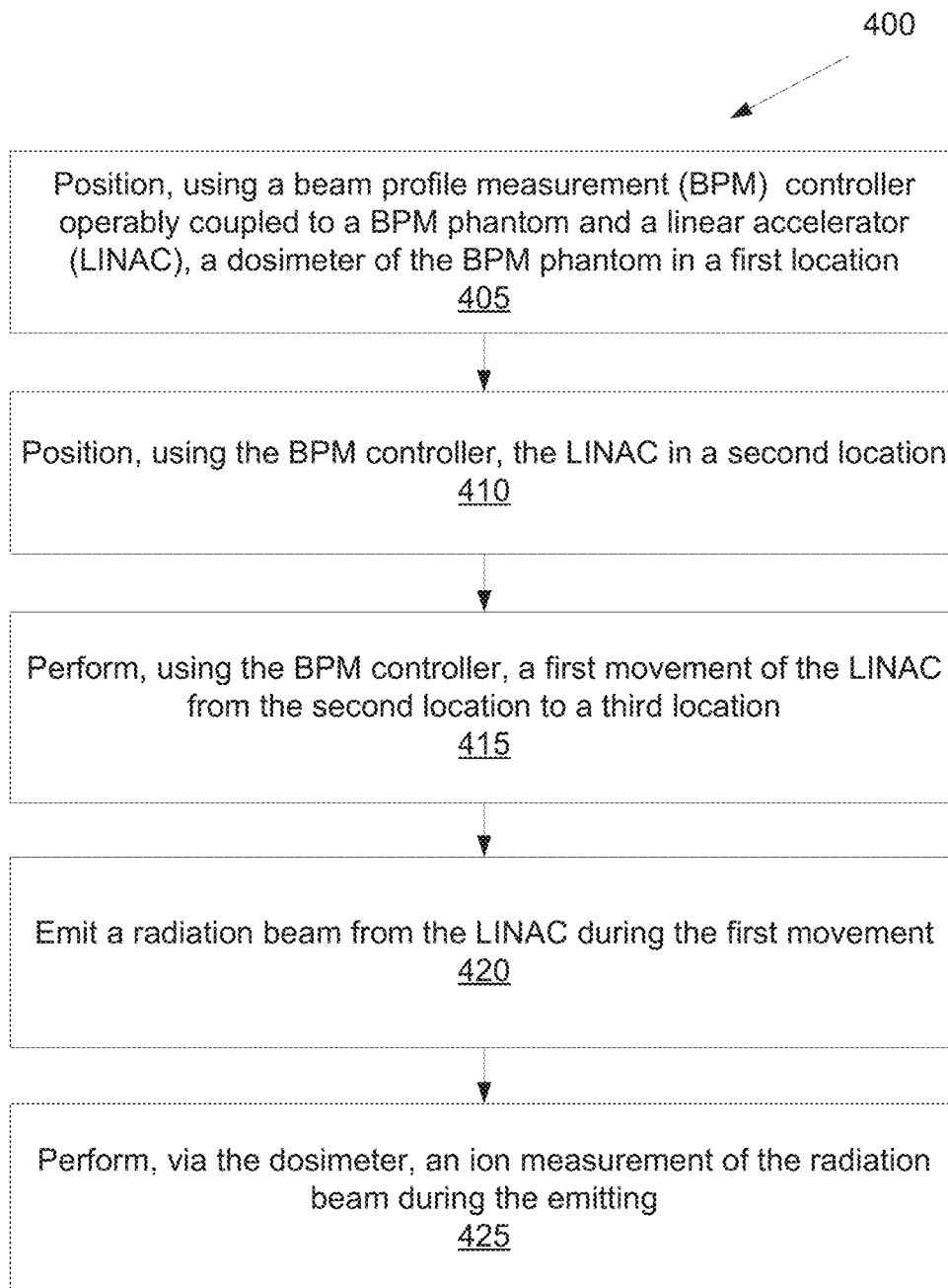
FIG. 4A illustrates a flow diagram of a method for measuring a beam profile of a radiation beam emitted using a LINAC coupled to a BPM controller, in accordance with implementations of the present disclosure.

FIG. 4A illustrates a flow diagram of a method 400 for measuring a beam profile of a radiation beam 150 emitted using a LINAC 130 coupled to a BPM controller 110, in accordance with implementations of the present disclosure. Method 400 is described in relation to measuring a beam profile when a LINAC 130 delivers radiation to a BPM phantom 120. However, it should be understood that method 400 may also be used to determine radiation delivered to a BPM phantom 120 by other systems that emit radiation, in particular, where the other system that emits radiation can be coupled to the BPM controller 110. The method 400 may be performed by processing logic that includes hardware (e.g., circuitry, dedicated logic, programmable logic, microcode, etc.), software (e.g., instructions run on a processing device to perform hardware simulation), or a combination thereof.

At block 405, processing logic positions, using a BPM controller 110 operably coupled to a BPM phantom 120 and a LINAC 130, a dosimeter 220 of the BPM phantom 120 in a first location. The processing logic positions the dosimeter 220 using the positioning device 230 (see FIGS. 2A-E). The processing logic causes the motor 236 to move the carriage 232 and the dosimeter 220 to the first location.

At block 410, the processing logic positions, using the BPM controller 110, the LINAC 130 in a second location. The processing logic positions the LINAC 130 using the robotic arm 140 (see FIG. 1) or LINAC controller 320 (see FIG. 3B).

At block 415, the processing logic performs, using the BPM controller 110, a first movement of the LINAC 130 from the second location to a third location. The second location to third location may be in a horizontal direction (see FIGS. 5A-C), in the vertical direction (see FIG. 7A-B), in a horizontal diagonal direction (see FIG. 8A), in a horizontal rotation direction (see FIG. 9A), in a horizontal rectangular direction (see FIG. 10A), or in a horizontal spiral direction (see FIG. 11). The second location and the third location may be the same location (the LINAC is stationary during the emitting; see FIGS. 6A-B).

At block 420, the processing logic emits a radiation beam 150 from the LINAC 130 during the first movement (e.g., of block 415). During the emitting of the radiation beam 150, the dosimeter 220 may be stationary or may be moving in a vertical direction.

At block 425, the processing logic performs, via the dosimeter 220, an ion measurement of the radiation beam 150 during the emitting (e.g., of block 420). In one implementation, the processing logic may be coupled to one or more sensors (e.g., pressure sensor, temperature sensor, a sensor for temperature and pressure measurement, etc.) that may be integrated to the LINAC 130 or BPM system 100 or may be standalone. The processing logic may determine an adjusted ion measurement of the radiation beam 150 in view of the ion measurement (block 425) and the one or more pressure and temperature measurements.

In one implementation, performing of the first movement (block 415) may include moving the LINAC 130 in a horizontal direction, where the dosimeter 220 is stationary during the emitting (block 420) (see FIG. 5).

In one implementation, the second location and the third location are the same location (e.g., the LINAC 130 is stationary), the method 400 may further include performing, using the BPM controller 110, a second movement of the dosimeter 220 in a vertical direction from the first location to a fourth location, and the emitting (block 420) of the radiation beam 150 from the LINAC 130 is during the second movement (see FIG. 6).

In one implementation, performing of the first movement (block 415) may include moving the LINAC in a vertical direction, the method 400 may further include the processing logic performing, using the BPM controller 110, a second movement of the dosimeter 220 in the vertical direction from the first location to a fourth location, where emitting (block 420) of the radiation beam 150 from the LINAC 130 is during the first movement and the second movement, the first movement and the second movement are simultaneous and substantially equal, and the BPM phantom 120 includes a tank 210 that is stationary during the emitting (block 420) (see FIG. 7).

In one implantation, performing of the first movement (block 415) may include moving the LINAC 130 in one or more horizontal diagonal directions, where the dosimeter 220 is stationary during the emitting (block 420), the emitting (e.g., emission) forms an irradiation field, performing of the ion measurement (block 425) includes comparing (e.g., includes a comparison of) a plurality of off-center ratio (OCR) measurements at a plurality of angles of the irradiation field to a radiation field of a round shape (see FIG. 8).

In one implementation, performing of the first movement (block 415) may include moving the LINAC 130 in a circular direction, where the dosimeter 220 is stationary during the emitting (block 420), the emitting forms an irradiation field, and performing of the ion measurement (block 425) includes comparing (e.g., includes a comparison of) a first edge of the irradiation field to a second edge of a radiation field of a round shape (see FIG. 9).

In one implementation, performing of the first movement (block 415) may include moving the LINAC 130 in a rectangular direction, where the dosimeter 220 is stationary during the emitting (block 420), the emitting forms an irradiation field, and the ion measurement is an edge of the irradiation field of a rectangle (see FIG. 10).

In one implementation, performing of the first movement (block 415) may include moving the LINAC 130 in a spiral direction, where the dosimeter 220 is stationary during the emitting (block 420) (see FIG. 11).

It should be noted that the above described operations are just one method of measuring a beam profile of a radiation beam 150 emitted and that, in alternative implementations, certain ones of the operations of FIG. 4A may be optional or take a simpler form.

Figure 4B:
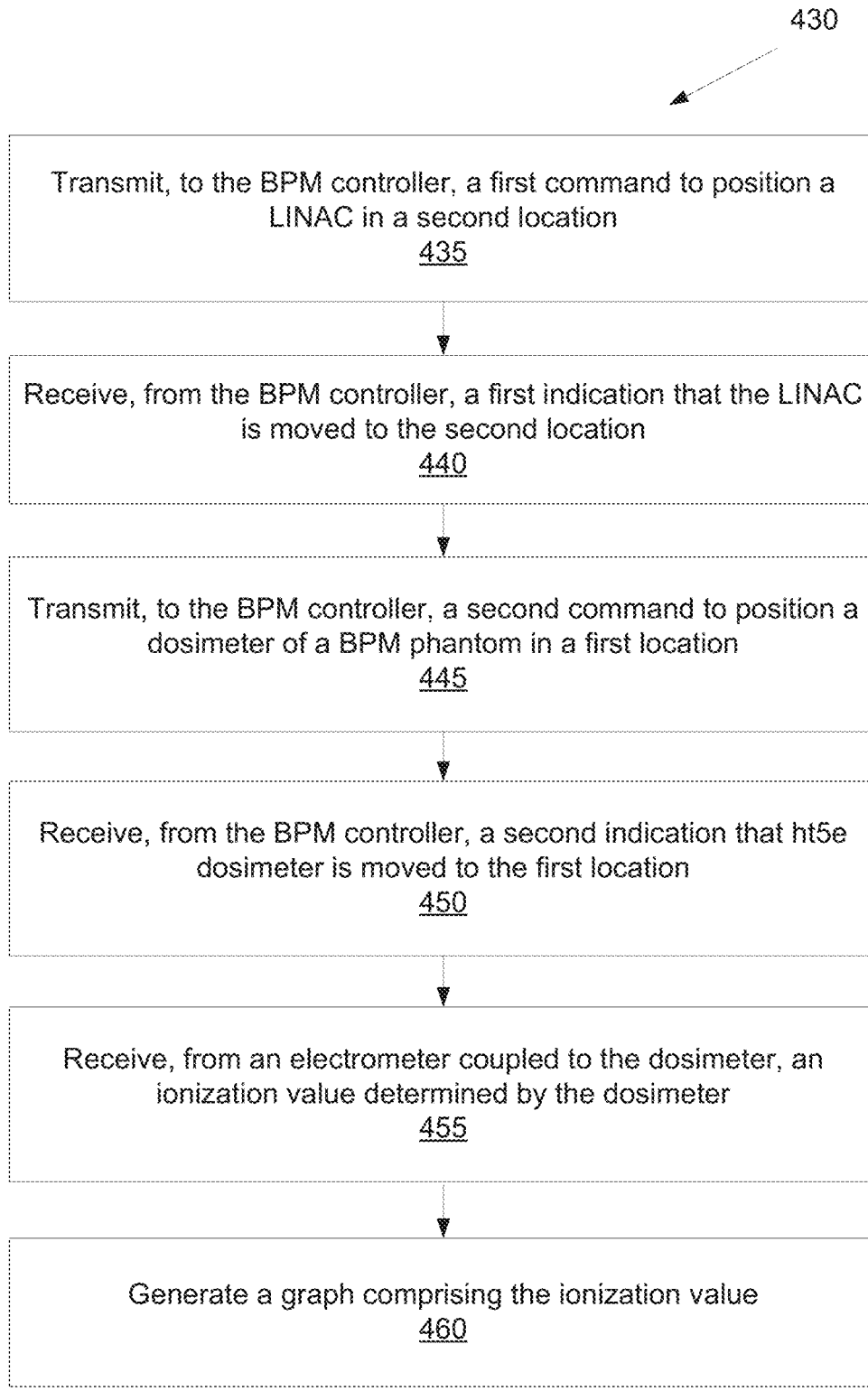
FIG. 4B illustrates a flow diagram of a method for measuring a beam profile of a radiation beam emitted using a LINAC coupled to a BPM controller, in accordance with implementations of the present disclosure.

FIG. 4B illustrates a flow diagram of a method 430 for measuring a beam profile of a radiation beam 150 emitted using a LINAC 130 coupled to a BPM controller 110, in accordance with implementations of the present disclosure. Method 430 is described in relation to measuring a beam profile when a LINAC 130 delivers radiation to a BPM phantom 120. However, it should be understood that method 430 may also be used to determine radiation delivered to a BPM phantom 120 by other systems that emit radiation, in particular, where the other system that emits radiation can be coupled to the BPM controller 110. The method 430 may be performed by processing logic that includes hardware (e.g., circuitry, dedicated logic, programmable logic, microcode, etc.), software (e.g., instructions run on a processing device to perform hardware simulation), or a combination thereof. In one implementation, method 430 is performed by BPM operation software operated on the processing device 300 of FIG. 3A or 3B.

At block 435, processing logic transmits, to a BPM controller 110, a first command to position a LINAC 130 in a second location (e.g., measurement position). The BPM controller 110 transmits, to the LINAC controller 320 (e.g., robot controller), the first command to position the LINAC 130 in the second location. The LINAC 130 is positioned in the second location in response to the LINAC controller 320 receiving the first command.

At block 440, processing logic receives, from the BPM controller 110, a first indication that the LINAC 130 is moved to the second location. The first indication is received by the BPM controller 110 from the LINAC controller 320.

At block 445, processing logic transmits, to the BPM controller 110, a second command to position a dosimeter 220 (e.g., ion chamber) of a BPM phantom 120 in a first location (e.g., measurement position). The BPM controller 110 transmits, to the BPM phantom 120 (e.g., positioning device 230), the second command to position the dosimeter 220 in the first location. The dosimeter 220 is positioned in the first location in response to the BPM phantom 120 receiving the second command.

At block 450, processing logic receives, from the BPM controller 110, a second indication that the dosimeter 220 is moved to the first location. The second indication is received by the BPM controller 110 from the BPM phantom 120.

At block 455, processing logic receives, from an electrometer 310 coupled to the dosimeter 220, an ionization value determined by the dosimeter 220. The ionization value is an ion measurement performed via the dosimeter 220 during emitting of a radiation beam 150 from the LINAC 130 during performing, using the BPM controller 110, a first movement of the LINAC 130 from the second location to a third location.

At block 460, processing logic generates a graph including the ionization value. In one implementation, the ionization value may be further in view of at least one of temperature measurements or pressure measurements. The at least one of temperature measurements or pressure measurements may be received by the processing logic from one or more sensors (e.g., pressure sensor, temperature sensor, a sensor for temperature and pressure measurement, etc.) that may be integrated to the LINAC 130 or BPM system 100 or may be standalone.

It should be noted that the above described operations are just one method of measuring a beam profile of a radiation beam 150 emitted and that, in alternative implementations, certain ones of the operations of FIG. 4B may be optional or take a simpler form.

FIGS. 5A-11 illustrate performing various beam profile measurements using the BPM system 100, in accordance with implementations of the present disclosure. In some implementations, the LINAC commissioning and QA beam data are obtained by one or more of the beam profile measurements of FIGS. 5A-11. The beam profile measurements of FIGS. 5A-11 may be in accordance with one or more of the Task Group 51 (TG-51 of the Radiation Therapy Committee of the American Association of Physicists in Medicine (AAPM); protocol for clinical reference dosimetry of high-energy photon and electron beams), Technical Report Series No. 398 (TRS-398 sponsored by International Atomic Energy Agency (IEAA), World Health Organization (WHO), Pan American Health Organization (PAHO), and European Society for Radiotherapy and Oncology (ES-TRO); absorbed dose determination in external beam radiotherapy; an international code of practice for dosimetry based on standards of absorbed dose to water), TG-106 (of the Therapy Physics Committee of the AAPM for properly measuring a set of beam data of the radiation beam 150 emitted from a LINAC), etc. Implementations disclosed herein are not limited to use only with the TG-51, TRS-398, and TG-106 guidelines.

FIGS. 5A-D illustrate performing an off-center ratio (OCR) measurement with the BPM system 100, in accordance with implementations of the present disclosure.

FIG. 5A is a side view, FIG. 5B is a front view, and FIG. 5C is a bottom view of the LINAC 130 emitting a radiation beam 150 to the BPM phantom 120 while the LINAC 130 performs a first movement and the dosimeter 220 is stationary (e.g., at one of a depth of 15 mm, 50 mm, 100 mm, 200 mm, 250 mm, 300 mm, etc. from the surface of the liquid, solid, or gas in the tank 210 to the dosimeter 220).

The BPM controller 110 positions the dosimeter 220 in a first position and the LINAC 130 in a second location, performs a first movement of the LINAC 130 from the second location to a third location, emits a radiation beam 150 from the LINAC 130 during the first movement, and performs, via the dosimeter, an ion measurement of the radiation beam 150 during the emitting. In the performing of the OCR measurement (FIGS. 5A-D), the dosimeter 220 remains stationary during the first movement and the first movement is one or more horizontal movements. The first movement includes one or more of the LINAC 130 moving in a first horizontal direction 510 (e.g., substantially perpendicular to the front and the back of the tank 210, substantially parallel to the first side and the second side of the tank 210) or moving in a second horizontal direction 520 (e.g., substantially perpendicular to the first side and the second side of the tank 210, substantially parallel to the front and the back of the tank 210).

FIG. 5D is a beam profile graph 530 for one or more OCR measurements, in accordance with implementations of the present disclosure. The direction of scanning is one or more of the first horizontal direction 510 or the second horizontal direction 520. The relative percentage is a ratio of the amount of radiation detected by the dosimeter 220 to the amount of radiation emitted by the LINAC 130. The beam profile graph 530 is a bell curve. In one implementation, the beam profile graph 530 may have a relative percentage of about 100% at 0 mm offset between the dosimeter 220 and the LINAC 130 (e.g., the radiation beam 150 emitted using the LINAC 130 is directly in line with the dosimeter 220). The beam profile graph 530 may have a relative percentage of about 90% at 20 mm offset, a relative percentage of about 70% at 30 mm offset, a relative percentage of about 5% at 40 mm offset, and so forth (e.g., the offset is a distance between the center of the radiation beam 150 emitted using the LINAC 130 and the center of the dosimeter 220).

FIGS. 6A-C illustrate performing a percentage depth dose (PDD) measurement with the BPM system 100, in accordance with implementations of the present disclosure. A PDD measurement is a ratio of a first absorbed dose of a radiation beam 150 at a depth to a second absorbed dose of a radiation beam 150 at a fixed reference depth (e.g., of maximum dose). The PDD measurement is calculated by dose at depth "d" divided by dose at maximum depth "$d_{max}$" (e.g., reference depth corresponding to maximum dose). Fixed source-to-surface distance (SSD) may be used for PDD measurements. The tank 210 location and the amount of liquid, solid, or gas in the tank 210 remain constant during the performing of the PDD measurement with the BPM system 100.

FIG. 6A is a side view and FIG. 6B is a front view of the LINAC 130 emitting a radiation beam 150 to the BPM phantom 120 while the LINAC 130 is stationary (e.g., LINAC 130 performs a first movement from a second location to a third location, where the second location and the third location are the same location) and the dosimeter 220 performs a second movement.

The BPM controller 110 positions the dosimeter 220 in a first location and the LINAC 130 in a second location, performs a second movement of the dosimeter 220 from the first location to a fourth location, emits a radiation beam 150 from the LINAC 130 during the second movement, and performs, via the dosimeter 220, an ion measurement of the radiation beam 150 during the emitting. In performing of the PDD measurement (FIGS. 6A-C), the LINAC 130 remains stationary during the second movement (e.g., performs a first movement from a second location to a third location, where the second location and the third location are the same location), and the second movement is a vertical movement 610. In performing of the PDD measurement, the tank 210 may also remain stationary.

FIG. 6C is a beam profile graph 620 for one or more PDD measurements, in accordance with implementations of the present disclosure. The direction of scanning is the vertical movement 610. The relative percentage is a ratio of the amount of radiation detected by the dosimeter 220 to the amount of radiation emitted by the LINAC 130. In one implementation, the beam profile graph 620 may have a relative percentage of about 55% when the dosimeter 220 has about 0 mm offset from the maximum height of the dosimeter 220 (e.g., the dosimeter 220 in a first position 222, see FIGS. 2A-B and 2D-E). The beam profile graph 620 may have a relative percentage of about 100% at a 15 mm offset, about 82% at a 50 mm, about 60% at 100 mm, about 42% at 150mm, about 30% at 200 mm, and so forth.

FIG. 7A-B illustrate performing a tissue phantom ratio (TPR) measurement or a tissue-maximum ratio (TMR) measurement with the BPM system 100, in accordance with implementations of the present disclosure. TPR or TMR are measured by keeping the source-to-detector distance (e.g., distance from LINAC 130 to dosimeter 220) constant and varying the depth of the dosimeter 220 in the BPM phantom 120. TPR (e.g., TPR 20/10) is a ratio of a first absorbed dose of a radiation beam 150 at a given point in a phantom to a second absorbed dose of the radiation beam 150 at the same point at a fixed reference depth (e.g., 5 cm, 10 cm). TMR is a TPR that has a reference depth that corresponds to a maximum dose of the radiation beam 150. TPR and TMR are measured at a constant surface-to-axis distance (SAD). The tank 210 location and the amount of liquid, solid, or gas in the tank 210 remain constant during the performing of the TPR or TMR measurement. The dosimeter 220 is moved by the positioning device 230 and not by the LINAC 130 (e.g., the dosimeter 220 is not housed in an attachment ("birdcage attachment") fastened to the LINAC).

FIG. 7A is a side view and FIG. 7B is a front view of the LINAC 130 emitting a radiation beam 150 to the BPM phantom 120 while the LINAC 130 performs a first movement and the dosimeter 220 performs a second movement.

The BPM controller 110 positions the dosimeter 220 in a first position and the LINAC 130 in a second location, performs a first movement of the LINAC 130 from the second location to a third location, performs a second movement of the dosimeter 220 from the first location to a fourth location, emits a radiation beam 150 from the LINAC 130 during the first movement and the second movement, and performs, via the dosimeter, an ion measurement of the radiation beam 150 during the emitting. In the performing of the PDD measurement (FIGS. 7A-B), the first movement is in a first vertical direction 710, the second movement is in a second vertical direction 720, the first movement and the second movement are simultaneous and substantially equal (e.g., the first and second movements are over substantially the same distance at substantially the same time and at substantially the same speed), and the tank 210 is stationary during the emitting.

FIGS. 8A-C illustrate performing a diagonal scan measurement with the BPM system 100, in accordance with implementations of the present disclosure.

FIG. 8A is a bottom view of the LINAC 130 emitting a radiation beam 150 to the BPM phantom 120 while the LINAC 130 performs a first movement and the dosimeter 220 is stationary.

The BPM controller 110 positions the dosimeter 220 in a first position and the LINAC 130 in a second location, performs a first movement of the LINAC 130 from the second location to a third location, emits a radiation beam 150 from the LINAC 130 during the first movement, and performs, via the dosimeter, an ion measurement of the radiation beam 150 during the emitting. In the performing of the diagonal scan measurement (FIGS. 8A), the dosimeter 220 remains stationary during the first movement, and the first movement is one or more horizontal diagonal movements. The first movement include the LINAC 130 moving in one or more horizontal diagonal directions (e.g., a first diagonal direction 810a, a second diagonal direction 810b, etc. (hereinafter diagonal directions 810). In one implementation, by performing the diagonal scan measurements, the OCR at multiple angles of the irradiation field of dodecagon (e.g., when using Iris collimator on the LINAC 130) may be verified and the OCR at an angle of the irradiation field of dodecagon can be compared to the radiation field of a round shape.

FIG. 8B illustrates a radiation field of a dodecagon including diagonal scans at different angles. The radiation field of the dodecagon includes a diagonal scan at a first angle 820a, a diagonal scan at a second angle 820b, and so forth.

FIG. 8C illustrates a radiation field of a round shape (e.g., circle) including the diagonal scans at different angles. The radiation field of the round shape includes the diagonal scan at the first angle 820a, the diagonal scan at the second angle 820b, and so forth.

The OCR measurements at one or more angles of the irradiation field of dodecagon in FIG. 8B are compared to the radiation field of the round shape of FIG. 8C to determine conformity of the radiation beam 150 emitted by the LINAC 130.

FIGS. 9A-C illustrate performing a rotation scan measurement with the BPM system 100, in accordance with implementations of the present disclosure.

FIG. 9A is a bottom view of the LINAC 130 emitting a radiation beam 150 to the BPM phantom 120 while the LINAC 130 performs a first movement and the dosimeter 220 is stationary.

The BPM controller 110 positions the dosimeter 220 in a first position and the LINAC 130 in a second location, performs a first movement of the LINAC 130 from the second location to a third location, emits a radiation beam 150 from the LINAC 130 during the first movement, and performs, via the dosimeter, an ion measurement of the radiation beam 150 during the emitting. In the performing of the rotation scan measurement (FIG. 9A), the dosimeter 220 remains stationary during the first movement, and the first movement is substantially circular in a horizontal plane. The first movement includes the LINAC 130 moving in a horizontal circular direction (e.g., a circular direction 910). In one implementation, by performing the rotation scan measurement, the edge of the irradiation field of dodecagon (e.g., when using Iris collimator on the LINAC 130) may be verified and the edge of the irradiation field of dodecagon may be compared to the edge of a radiation field of a round shape.

FIG. 9B illustrates a radiation field of a dodecagon including a rotation scan 920. FIG. 9C illustrates a radiation field of a round shape (e.g., circle) including the rotation scan 920. The edge of the irradiation field of dodecagon in FIG. 9B is compared to the edge of the round shape of FIG. 9C to determine conformity of the radiation beam 150 emitted by the LINAC 130.

FIGS. 10A-B illustrate performing a rectangle scan measurement with the BPM system 100, in accordance with implementations of the present disclosure.

FIG. 10A is a bottom view of the LINAC 130 emitting a radiation beam 150 to the BPM phantom 120 while the LINAC 130 performs a first movement and the dosimeter 220 is stationary.

The BPM controller 110 positions the dosimeter 220 in a first position and the LINAC 130 in a second location, performs a first movement of the LINAC 130 from the second location to a third location, emits a radiation beam 150 from the LINAC 130 during the first movement, and performs, via the dosimeter, an ion measurement of the radiation beam 150 during the emitting. In the performing of the rectangle scan measurement (FIG. 10A), the dosimeter 220 remains stationary during the first movement, and the first movement is substantially a rectangle in a horizontal plane. The first movement may include the LINAC 130 moving in a horizontal rectangular direction (e.g., a rectangular direction 1010).

FIG. 10B illustrates a radiation field (e.g., formed by the emitting of the radiation beam 150) of a rectangle including a rectangle scan 1020 (e.g., scan of the edges of the radiation field, etc.). In one implementation, by performing the rectangle scan measurement, the edge of the irradiation field of rectangle (e.g., when using a multi-leaf collimator (MLC) collimator on the LINAC 130) may be verified.

FIG. 11 illustrates performing a spiral scan measurement with the BPM system 100, in accordance with implementations of the present disclosure.

FIG. 11 is a bottom view of the LINAC 130 emitting a radiation beam 150 to the BPM phantom 120 while the LINAC 130 performs a first movement and the dosimeter 220 is stationary.

The BPM controller 110 positions the dosimeter 220 in a first position and the LINAC 130 in a second location, performs a first movement of the LINAC 130 from the second location to a third location, emits a radiation beam 150 from the LINAC 130 during the first movement, and performs, via the dosimeter, an ion measurement of the radiation beam 150 during the emitting. In the performing of the rectangle scan measurement (FIG. 11A), the dosimeter 220 remains stationary during the first movement, and the first movement is substantially a spiral (e.g., helical, etc.) in a horizontal plane. The first movement may include the LINAC 130 moving in a horizontal spiral direction (e.g., a spiral direction 1110).

FIG. 12 illustrates systems that may be used in performing radiation treatment, in accordance with implementations of the present disclosure. These systems may be used to perform, for example, the methods described above. As described below and illustrated in FIG. 12, a system 1200 may include a BPM system 100 and a treatment delivery system 1215.

BPM system 100 includes a processing device 1240 to generate and modify beam profile measurements. In one implementation, processing device may be the same as processing device 300 of FIG. 3A or FIG. 3B. Processing device 1240 may represent one or more general-purpose processors (e.g., a microprocessor), special purpose processor such as a digital signal processor (DSP) or other type of device such as a controller or field programmable gate array (FPGA). Processing device 1240 may be configured to execute instructions for performing beam profile measurement generating operations discussed herein.

BPM system 100 may also include system memory 1235 that may include a random access memory (RAM), or other dynamic storage devices, coupled to processing device 1240 by bus 1286, for storing information and instructions to be executed by processing device 1240. System memory 1235 also may be used for storing temporary variables or other intermediate information during execution of instructions by processing device 1240. System memory 1235 may also include at least one of a read only memory (ROM) or other static storage device coupled to bus 1286 for storing static information and instructions for processing device 1240.

BPM system 100 may also include storage device 1245, representing one or more storage devices (e.g., a magnetic disk drive or optical disk drive) coupled to bus 1286 for storing information and instructions. Storage device 1245 may be used for storing instructions for performing the beam profile measurement steps discussed herein.

Processing device 1240 may also be coupled to a display device 1250, such as a cathode ray tube (CRT) or liquid crystal display (LCD), for displaying information (e.g., beam profile graph 530 of FIG. 5D, beam profile graph 620 of FIG. 6C, etc.) to the user. An input device 1255, such as a keyboard, may be coupled to processing device 1240 for communicating at least one of information or command selections to processing device 1240. One or more other user input devices (e.g., a mouse, a trackball or cursor direction keys) may also be used to communicate directional information, to select commands for processing device 1240 and to control cursor movements on display 1250. Processing device 1240 may be coupled to system memory 1235, storage device 1245, display device 1250, and input device 1255 by a bus 1286 or other type of control and communication interface.

In one implementation, the input device 1255 may receive input from a user to perform one or more beam profiling measurements (e.g., for commissioning, for QA, etc.). The processing device 1240 may transmit a command to BPM controller 110 to perform the one or more beam profiling measurements. The BPM controller 110 may position a dosimeter 220 in a first location, position a LINAC 130 in a second location, perform a first movement of the LINAC 130 from the second location to a third location, and emit a radiation beam 150 using the LINAC 130 during the first movement. The processing device 1240 may receive an ion measurement from the dosimeter 220 of the radiation beam 150 during the first movement (e.g., via BPM controller 110 (see FIG. 3A), via electrometer 310 (see FIG. 3B), etc.). The processing device 1240 may generate information from the ion measurement (e.g., beam profile graph 530 of FIG. 5D, beam profile graph 620 of FIG. 6C, etc.) to be displayed via display device 1250.

BPM system 100 may share its database (e.g., data stored in storage 1245) with a treatment delivery system, such as treatment delivery system 1215, so that it may not be necessary to export from the treatment planning system prior to treatment delivery. BPM system 100 may be linked to treatment delivery system 1215 via a data link 1290, which in one implementation may be a direct link, a LAN link or a WAN link.

In one implementation, treatment delivery system 1215 includes one or more of a therapeutic or surgical radiation source 1260 (e.g., LINAC 130) to administer a prescribed radiation dose (e.g., radiation beam 150) to a target volume (e.g., patient, BPM phantom 120, etc.). Treatment delivery system 1215 may also include imaging system 1265 to perform computed tomography (CT) such as cone beam CT, and images generated by imaging system 1265 may be two-dimensional (2D) or three-dimensional (3D).

Treatment delivery system 1215 may also include a processing device 1270 to control radiation source 1260, receive and process data from BPM system 100, and control a patient support device such as a treatment couch 1275. Processing device 1270 may include one or more general-purpose processors (e.g., a microprocessor), a special purpose processor such as a digital signal processor (DSP) or other type of device such as a controller or field programmable gate array (FPGA). The processing device 1270 may be configured to execute instructions to position the LINAC 130.

Treatment delivery system 1215 also includes system memory such as a random access memory (RAM), or other dynamic storage devices, coupled to a processing device, for storing information and instructions to be executed by the processing device. The system memory also may be used for storing temporary variables or other intermediate information during execution of instructions by the processing device 1270 (e.g., instructions received from BPM system 100) or processing device 1240. The system memory may also include one or more of a read only memory (ROM) or other static storage device for storing static information and instructions for the processing device.

Treatment delivery system 1215 also includes a storage device, representing one or more storage devices (e.g., a magnetic disk drive or optical disk drive) for storing information and instructions (e.g., instructions received from BPM system 100). Processing device 1270 may be coupled to radiation source 1260 and treatment couch 1275 by a bus 1292 or other type of control and communication interface.

Processing device 1270 may implement methods to manage timing of diagnostic x-ray imaging in order to maintain alignment of a target with a radiation treatment beam delivered by the radiation source 1260.

In one implementation, the treatment delivery system 1215 includes an input device 1278 and a display 1277 connected with processing device 1270 via bus 1292. The display 1277 can show trend data that identifies a rate of target movement (e.g., a rate of movement of a target volume that is under treatment). The display 1277 can also show a current radiation exposure of a patient and a projected radiation exposure for the patient. The input device 1278 can enable a clinician to adjust parameters of a treatment delivery plan during treatment.

It should be noted that when data links 1286 and 1290 are implemented as LAN or WAN connections, at least one of BPM system 100 or treatment delivery system 1215 may be in decentralized locations such that the systems may be physically remote from each other. Alternatively, at least one of BPM system 100 or treatment delivery system 1215 may be integrated with each other in one or more systems.

FIG. 13 illustrates a gantry based intensity modulated radiotherapy (IMRT) system 1300, in accordance with implementations of the present disclosure. In one implementation, the LINAC 130 is mounted on a gantry 1303. In a gantry based system 1300, a radiation source (e.g., a LINAC 130) having a head assembly 1301 are mounted on a gantry 1303 in such a way that they rotate in a plane corresponding to an axial slice of the patient. Radiation is then delivered from several positions on the circular plane of rotation. In IMRT, the BPM controller 110 may position the LINAC 130 in a second position and perform a first movement of the LINAC 130 by moving the LINAC via the gantry 1303 and head assembly 1301 of the gantry based system 1300. The resulting system generates arbitrarily shaped treatment beams that intersect each other at the isocenter to deliver a dose distribution to the target location. In one implementation, the gantry based system 1300 may be a c-arm based system.

FIG. 14 illustrates a tomotherapy radiotherapy system 1400, in accordance with implementations of the present disclosure. Tomotherapy is a type of radiation therapy which uses a narrow intensity modulated pencil beam (i.e., radiation beam 150) to deliver radiation to a target region (e.g., a tumor, patient, BPM phantom 120, etc.). The tomotherapy radiotherapy system 1400 includes a LINAC 130 mounted to a ring gantry 1420. The ring gantry 1420 has a toroidal shape and the target region (e.g., BPM phantom 120, a patient, etc.) is moved through a bore of the toroidal shape of the ring gantry 1420. A central axis passes through the center of the bore. In one implementation, a radiation beam 150 is generated by a LINAC 130 that is mounted to a ring gantry 1420 that rotates around the central axis to deliver the radiation beam 150 to a BPM phantom 120 from various angles. While the radiation beams 150 are being delivered, the BPM phantom 120 is on a treatment couch 1440 (e.g., an adjustable table) and the BPM phantom 120 is simultaneously moved through the bore of the ring gantry 1420 allowing horizontal movement of the radiation beam 150 in relation to the dosimeter 220 without horizontally moving the LINAC 130 or the dosimeter 220. For example, to perform the OCR measurement of FIGS. 5A-D, the LINAC 130 remains stationary and the treatment couch 1440 moves the BPM phantom 120 in a horizontal direction.

In some implementations, the LINAC 130 may be mounted to a C-arm gantry in a cantilever-like manner, which rotates the LINAC 130 about the axis passing through the isocenter of the ring gantry 1420. In other implementations, the LINAC 130 may be mounted to a robotic arm having multiple (e.g., 5 or more) degrees of freedom in order to position the LINAC 130 around the ring gantry 1420 to irradiate the dosimeter 220 in the BPM phantom 120 that is moved horizontally by the treatment couch 1440.

It will be apparent from the foregoing description that aspects of the present disclosure may be embodied, at least in part, in software. That is, the techniques may be carried out in a computer system or other data processing system in response to a processing device 300 or 1240 (see FIGS. 3A-B and 12), for example, executing sequences of instructions contained in a memory. In various implementations, hardware circuitry may be used in combination with software instructions to implement the present disclosure. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by processing device 300 or 1240.

A machine-readable medium can be used to store software and data which when executed by a general purpose or special purpose data processing system causes the system to perform various methods of the present disclosure. This executable software and data may be stored in various places including, for example, system memory and storage or any other device that is capable of storing at least one of software programs or data. Thus, a machine-readable medium includes any mechanism that provides (i.e., stores) information in a form accessible by a machine (e.g., a computer, network device, personal digital assistant, manufacturing tool, any device with a set of one or more processors, etc.). For example, a machine-readable medium includes recordable/non-recordable media such as read only memory (ROM), random access memory (RAM), magnetic disk storage media, optical storage media, flash memory devices, etc. The machine-readable medium may be a non-transitory computer readable storage medium.

Unless stated otherwise as apparent from the foregoing discussion, it will be appreciated that terms such as "receiving," "positioning," "performing," "emitting," "causing," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Implementations of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present disclosure are not described with reference to any particular programming language. It will be appreciated that a variety of programming languages may be used to implement implementations of the present disclosure.

It should be noted that the methods and apparatus described herein are not limited to use only with medical diagnostic imaging and treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, the disclosure has been described with reference to specific exemplary implementations thereof. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense.

What is claimed is:

1. A method comprising:
positioning, using a beam profile measurement (BPM) controller operably coupled to a BPM phantom and a linear accelerator (LINAC), a dosimeter of the BPM phantom in a first location;
positioning, using the BPM controller, the LINAC in a second location;

performing, using the BPM controller, a first movement of the LINAC from the second location to a third location, wherein performing of the first movement comprises moving the LINAC in one or more horizontal diagonal directions;
emitting a radiation beam from the LINAC during the first movement of the LINAC from the second location to the third location; and
performing, via the dosimeter, an ion measurement of the radiation beam during the emitting.

2. The method of claim 1, wherein:
the dosimeter is stationary during the emitting;
the emitting forms an irradiation field; and
the performing of the ion measurement comprises comparing a plurality of off-center ratio (OCR) measurements at a plurality of angles of the irradiation field to a radiation field of a round shape.

3. The method of claim 1, wherein:
the performing of the first movement comprises moving the LINAC in a circular direction;
the dosimeter is stationary during the emitting;
the emitting forms an irradiation field; and
the performing of the ion measurement comprises comparing a first edge of the irradiation field to a second edge of a radiation field of a round shape.

4. The method of claim 1, wherein:
the performing of the first movement comprises moving the LINAC in a rectangular direction;
the dosimeter is stationary during the emitting;
the emitting forms an irradiation field; and
the ion measurement is an edge of the irradiation field of a rectangle.

5. The method of claim 1, wherein:
the performing of the first movement comprises moving the LINAC in a spiral direction; and
the dosimeter is stationary during the emitting.

6. The method of claim 1, wherein:
the performing of the first movement comprises moving the LINAC in a vertical direction;
the method further comprises performing, using the BPM controller, a second movement of the dosimeter in the vertical direction from the first location to a fourth location;
the emitting of the radiation beam from the LINAC is during the first movement and the second movement; and
the first movement and the second movement are simultaneous and substantially equal.

7. A non-transitory computer readable storage medium having instructions that, when executed by a processing device, cause the processing device to:
cause a dosimeter of a beam profile measurement (BPM) phantom to be positioned in a first location;
cause a linear accelerator (LINAC) to be positioned in a second location;
cause a first movement of the LINAC from the second location to a third location;
cause the LINAC to emit a radiation beam during the first movement of the LINAC from the second location to the third location; and
receive, from the dosimeter, an ion measurement of the radiation beam during the first movement, wherein the ion measurement comprises a comparison of a first edge of the irradiation field to a second edge of a radiation field of a round shape.

8. The non-transitory computer readable storage medium of claim 7, wherein:
the first movement comprises moving the LINAC in a circular direction;
the dosimeter is stationary during the ion measurement;
emission of the radiation beam forms an irradiation field.

9. The non-transitory computer readable storage medium of claim 7, wherein the processing device further to cause movement of the LINAC in a rectangular direction, and wherein:
the dosimeter is stationary during the ion measurement;
emission of the radiation beam forms an irradiation field; and
the ion measurement is an edge of the irradiation field of a rectangle.

10. The non-transitory computer readable storage medium of claim 7, wherein the processing device further to cause movement of the LINAC in a spiral direction, and wherein:
the dosimeter is stationary during the ion measurement.

11. The non-transitory computer readable storage medium of claim 7, wherein the processing device further to cause movement of the LINAC in a vertical direction, and wherein:
the processing device is further to cause a second movement of the dosimeter in the vertical direction from the first location to a fourth location;
emission of the radiation beam from the LINAC is during the first movement and the second movement;
the first movement and the second movement are substantially equal; and
the BPM phantom comprises a tank that is stationary during the emitting.

12. A beam profile measurement (BPM) system comprising:
a BPM phantom comprising:
a tank to house a liquid;
a dosimeter disposed in the tank, wherein the dosimeter is to detect ionization of a radiation beam emitted from a linear accelerator (LINAC); and
a positioning device to move the dosimeter in a vertical direction; and
a BPM controller o operably couple to the BPM phantom and the LINAC, the BPM controller to:
position the dosimeter in a first location;
position the LINAC in a second location;
perform a first movement of the LINAC from the second location to a third location;
emit the radiation beam using the LINAC during the first movement of the LINAC from the second location to the third location; and
receive, from the dosimeter, an ion measurement of the radiation beam during the first movement;
one or more environmental sensors operatively coupled with the BPM controller, the BPM controller further to:
receive, from the one or more environmental sensors, one or more ambient pressure and temperature measurements;
adjust the ion measurement of the radiation beam received from the dosimeter in view of the one or more ambient pressure and temperature measurements; and
receive, from the one or snore environmental sensors, one or more location measurements of the LINAC relative to the BPM system, wherein positioning of the LINAC is in view of the one or more location measurements.

13. The BPM system of claim 12, the positioning device is to move the dosimeter from about 15 millimeters (mm) to about 200 mm below an upper surface of the liquid in the tank.

14. The BPM system of claim 12, wherein the dosimeter is an ionization chamber.

15. The BPM system of claim 12, wherein the positioning device comprises a motor coupled to a carriage to provide a second movement of the dosimeter in the vertical direction.

16. The BPM system of claim 12, wherein the dosimeter is coupled to an electrometer to amplify the ion measurement of the radiation beam.

* * * * *